(12) United States Patent
Odidi

(10) Patent No.: US 10,561,602 B2
(45) Date of Patent: Feb. 18, 2020

(54) CONTROLLED EXTENDED RELEASE PREGABALIN

(71) Applicant: Isa Odidi, Toronto (CA)

(72) Inventor: Isa Odidi, Toronto (CA)

(*) Notice: Subject to any disclaimer, the term of this patent is extended or adjusted under 35 U.S.C. 154(b) by 0 days.

(21) Appl. No.: 15/503,856

(22) PCT Filed: May 26, 2016

(86) PCT No.: PCT/CA2016/050597
§ 371 (c)(1),
(2) Date: Feb. 14, 2017

(87) PCT Pub. No.: WO2016/187718
PCT Pub. Date: Dec. 1, 2016

(65) Prior Publication Data
US 2017/0273896 A1 Sep. 28, 2017

Related U.S. Application Data

(60) Provisional application No. 62/166,324, filed on May 26, 2015.

(51) Int. Cl.
| | | |
|---|---|---|
| *A61K 31/16* | (2006.01) | |
| *A61K 9/00* | (2006.01) | |
| *A61K 45/06* | (2006.01) | |
| *A61K 9/16* | (2006.01) | |
| *A61K 31/19* | (2006.01) | |

(52) U.S. Cl.
CPC .......... *A61K 9/0002* (2013.01); *A61K 9/1676* (2013.01); *A61K 31/16* (2013.01); *A61K 31/19* (2013.01); *A61K 45/06* (2013.01); *A61K 9/0056* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,563,175 A | 10/1996 | Silverman et al. |
| 5,599,973 A | 2/1997 | Silverman et al. |
| 5,608,090 A | 3/1997 | Silverman et al. |
| 5,616,793 A | 4/1997 | Huckabee et al. |
| 5,629,447 A | 5/1997 | Huckabee et al. |
| 5,637,767 A | 6/1997 | Grote et al. |
| 5,684,189 A | 11/1997 | Silverman et al. |
| 5,710,304 A | 1/1998 | Silverman et al. |
| 5,840,956 A | 11/1998 | Grote et al. |
| 6,001,876 A | 12/1999 | Singh |
| 6,028,214 A | 2/2000 | Silverman et al. |
| 6,046,353 A | 4/2000 | Grote et al. |
| 6,117,906 A | 9/2000 | Silverman et al. |
| 6,197,819 B1 | 3/2001 | Silverman et al. |
| 2007/0269511 A1* | 11/2007 | Bockbrader ......... A61K 9/0065 424/468 |
| 2010/0092549 A1* | 4/2010 | Blundell ............... A61K 9/2072 424/456 |
| 2012/0009261 A1 | 1/2012 | Sesha |

FOREIGN PATENT DOCUMENTS

| | | |
|---|---|---|
| WO | 9959572 A1 | 11/1999 |
| WO | 9959573 A1 | 11/1999 |
| WO | 2006/078811 A2 | 7/2006 |

OTHER PUBLICATIONS

Intellipharmaceutics (Oct. 22, 2014; NPL document 1 of IDS filed Feb. 14, 2017) (Year: 2014).*
Intellipharmaceutics (Oct. 22, 2014; NPL document 1 of IDS dated Feb. 14, 2017) (Year: 2014).*
T.Z. Su, M.R. Feng, M.L. Weber, Mediation of Highly Concentrative Uptake of Pregabalin by L-Type Amino Acid Transport in Chinese Hamster Ovary and Caco-2 Cells, J Pharmacol Exp Ther (2005), vol. 313; pp. 1406-1415.
Intellipharmaceutics Reports Positive Results From a Series of Phase I Clinical Trials of Regabatin(TM) XR (Pregabalin Extended-Release), Oct. 22, 2014, Retrieved from Internet: http://www.intellipharmaceutics.com/releasedetail.cfm?releaseid=877655.
The International Search Report and the Written Opinion of the International Searching Authority, dated Aug. 31, 2016, for PCT/CA2016/050597, filed on May 26, 2016.
European Search Report, dated Dec. 14, 2018, Application No./Patent No. 16799000.1-1109 / 3302425 PCT/CA2016050597.
Canadian Patent Office Requisition dated Jul. 12, 2019, for Canadian Patent Application No. 2,953,225.

* cited by examiner

*Primary Examiner* — Daniel M Podgorski
(74) *Attorney, Agent, or Firm* — Renner Kenner Greive Bobak Taylor and Weber

(57) ABSTRACT

A controlled extended release composition comprising at least one unit dosage form having at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof. Methods and uses of the composition are provided.

48 Claims, 14 Drawing Sheets

CONTROLLED EXTENDED RELEASE PREGABALIN

FIELD

The subject application relates generally to compositions and methods for controlled extended release of pregabalin and/or its derivatives/forms, in particular to compositions, methods, and uses thereof, and methods for making same.

BACKGROUND

Pregabalin is described as (S)-3-(aminomethyl)-5-methylhexanoic acid, binds to the calcium channel alpha-2-delta (α2δ) subunit and is an analog of endogenous inhibitory neurotransmitter gamma-amino butyric acid (GABA), which is involved in brain neuronal activity. The molecular formula is $C_8H_{17}NO_2$ and the molecular weight is 159.23 g/mol. Pregabalin is a white to off-white crystalline solid with a $pK_{a1}$ of about 4.2 and a $pK_{a2}$ of about 10.6. It is freely soluble in water and both basic and acidic aqueous solutions. The log of the partition coefficient (n-octanol/0.05 M phosphate buffer) at pH 7.4 is about −1.35.

In the U.S. and Canada, pregabalin has been approved for the management of neuropathic pain associated with diabetic peripheral neuropathy, management of post herpetic neuralgia, management of fibromyalgia, and as an adjunctive therapy for adult patients with partial onset seizures. Pregabalin is useful as antiseizure therapy for central nervous system disorders such as epilepsy, Huntington's chorea, cerebral ischemia, Parkinson's disease, tardive dyskinesia, and spasticity. Pregabalin exhibits anti-seizure activity and is useful for treating, among other conditions, epilepsy, pain, physiological conditions associated with psychomotor stimulants, inflammation, gastrointestinal (GI) damage, alcoholism, insomnia, fibromyalgia, and various psychiatric disorders, including anxiety, depression, mania, and bipolar disorder.

Pregabalin is currently available as immediate release LYRICA™ in 25, 50, 75, 100, 150, 200, 225, and 300 mg hard shell capsules and is administered in patients two or three times daily (BID or TID).

The recommended dose of pregabalin is 100 mg three times a day (300 mg/day) for the treatment of neuropathic pain associated with diabetic peripheral neuropathy and post herpetic neuralgia.

In the management of fibromyalgia, the recommended dose of LYRICA™ is 300 to 450 mg/day. Begin dosing at 75 mg two times a day (150 mg/day). The dose may be increased to 150 mg two times a day (300 mg/day) within 1 week based on efficacy and tolerability. Pregabalin at doses of 150 to 600 mg/day is recommended for adjunctive therapy for adult patients with partial onset seizures.

Pregabalin is described in U.S. Pat. No. 6,197,819. Further, U.S. Pat. No. 6,197,819 also has a generic disclosure of pharmaceutical compositions comprising pregabalin. U.S. Pat. No. 5,563,175 describes the use of pregabalin in the treatment of seizure disorders. U.S. Pat. No. 6,117,906 discloses the use of pregabalin in treating anxiety, while U.S. Pat. No. 6,001,876 discloses its use in treating pain. U.S. Pat. Nos. 6,663,175, 5,599,973, 5,608,090, 5,684,189, 5,710,304, 5,616,793, 5,629,447, 5,637,767, 5,840,956, 6,046,353, 6,028,214 disclose processes for preparation of pregabalin and intermediates used in these processes.

Pregabalin absorption in the GI tract has a specific and short window. Most, if not all, of the known formulations are aimed primarily at gastro-retention or flotation as a pivotal means of maintaining a sustained drug release albeit applying a different polymer construct.

Gastro-retentive drug delivery may be classified into three systems, i.e., an expansion-by-swelling system, a floating or buoyant system, and a bioadhesive system. All these approaches involve the use of swelling and expanding for achieving gastric retention. These systems are usually monolithic tablets and are comprised of the drug and one or more swellable polymers. These polymers swell unrestrained via imbibition of gastric fluid to such an extent that it causes the tablet to float on gastric contents.

Furthermore, for highly soluble drugs, controlled delivery systems, which utilize hydrophilic, polymeric matrices, do not provide adequate control over the drug release rate, instead resulting in a release that approximates first-order kinetics.

There is a need for alternative therapies to overcome or mitigate at least one of the deficiencies of the prior art or to at least provide patients with a useful alternative.

SUMMARY

In accordance with an aspect, there is provided a controlled extended release composition comprising at least one unit dosage form having at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

In an aspect, the composition is a once- or twice-a-day controlled extended release composition that provides higher exposure to at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, compared to LYRICA™ (pregabalin) immediate release composition taken two times-a-day.

In an aspect, the composition provides higher exposure to at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, at least within about the first twelve hours of administration, compared to LYRICA™ (pregabalin) immediate release composition taken two times-a-day.

In an aspect, the composition has a similar bioequivalency to LYRICA™ administered twice-a-day.

In an aspect, the composition provides chronotherapeutic controlled extended release.

In an aspect, the composition is for administration under at least one of fasting conditions and following, during or after a meal.

In an aspect, the composition is for administration during the meal.

In an aspect, said at least one unit dosage form comprises a core and, optionally, one or more coats.

In an aspect, the diameter of the core of said at least one unit dosage form is between about 0.001 mm and about 4 mm.

In an aspect, the composition described herein further comprises at least one other API, wherein the at least one other API is in the same unit dosage form(s) as the unit dosage form(s) comprising the at least one API or in a separate unit dosage form(s).

In an aspect, said at least one unit dosage form comprises a core and, optionally, one or more coats, wherein the at least one API and/or the at least one other API are in the core and/or coat(s).

In an aspect, the at least one other API is selected from the group consisting of antidepressants, muscle relaxants, anti-spasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

In an aspect, the composition does not promote undesirable lactam formation.

In an aspect, the at least one unit dosage form comprises at least two unit dosage forms.

In an aspect, each unit dosage form has predetermined distinct timed drug release characteristics and/or dissolution/rate profiles.

In an aspect, the at least one unit dosage form comprises at least one population of unit dosage forms.

In an aspect, the at least one unit dosage form comprises (i) a unit dosage form and (ii) at least one population of unit dosage forms.

In an aspect, the unit dosage form of (i) and each population of unit dosage forms of (ii) have distinct timed drug release characteristics and/or dissolution/rate profiles.

In an aspect, each population of (ii) is intermixed and/or physically separate from (a) another population of unit dosage forms and/or (b) the unit dosage form of (i).

In an aspect, the at least one unit dosage form comprises (i) at least two unit dosage forms, wherein one or more unit dosage forms have distinct timed drug release characteristics and/or dissolution/rate profile from one or more other unit dosage forms; and (ii) at least one population of unit dosage forms.

In an aspect, the at least two unit dosage forms of (i) and each population of unit dosage forms of (ii) have distinct timed drug release characteristics and/or dissolution/rate profiles.

In an aspect, each population of (ii) is intermixed and/or physically separate from (a) another population of unit dosage forms and/or (b) the at least two unit dosage form of (i).

In an aspect, drug release is via a multiple-phase trigger mechanism.

In an aspect, the multiple-phase trigger mechanism is a three-phase trigger mechanism.

In an aspect, the composition provides multiple site-specific delivery of at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

In an aspect, the composition provides multiple site-specific delivery in a rapid, delayed and controlled extended release manner in the GI tract, resulting in high exposure to at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

In an aspect, multiple site-specific delivery in the GI tract comprises delivery in the upper small intestine where most of L-amino acid transporters reside, but not beyond the hepatic flexure.

In an aspect, the at least one unit dosage forms comprise at least one pH-dependent unit dosage form and at least one pH-independent unit dosage form.

In an aspect, the at least one unit dosage form comprises at least two populations of unit dosage forms.

In an aspect, the at least two populations of unit dosage forms comprise a first population of unit dosage forms and a second population of unit dosage forms.

In an aspect, at least one of said first population of unit dosage forms and said second population of unit dosage forms comprise said at least one API.

In an aspect, said first population of unit dosage forms and said second population of unit dosage forms comprise said at least one API.

In an aspect, said first population of unit dosage forms comprise said at least one API and said second population of unit dosage forms comprise said at least one other API.

In an aspect, the composition described herein further comprises a third population of unit dosage forms comprising said at least one other API.

In an aspect, said first population of unit dosage forms has distinct timed drug release characteristics and/or dissolution/rate profiles compared to said second population of unit dosage forms.

In an aspect, said first population of unit dosage forms is intermixed and/or physically separate from said second population of unit dosage forms.

In an aspect, release of said at least one API from said first population of unit dosage forms depends on the pH of the surrounding environment.

In an aspect, the release is at a pH greater than about 5.0.

In an aspect, said first population of unit dosage forms is coated with at least one pH-dependent coat.

In an aspect, the pH-dependent coat is selected from the group consisting of cellulose esters, polyvinyl acetate phthalate, methacrylic acid copolymer type A, methacrylic acid copolymer type B, methacrylic acid copolymer type C, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, Chitosan, Shellac, cellulose acetate trimellitate, zein, derivatives thereof, and combinations thereof.

In an aspect, release of said at least one API from said second population of unit dosage forms is independent of pH of the surrounding environment.

In an aspect, the release is stepwise and pH-independent.

In an aspect, said second population of unit dosage forms is coated with at least one pH-independent coat.

In an aspect, said at least one pH-independent coat is selected from the group consisting of ethylcellulose, ammonium methacrylate copolymer, ethyl acrylate and methyl methacrylate copolymer, derivatives thereof, and combinations thereof.

In an aspect, the first population of unit dosage forms releases about 10% to about 90% of said at least one API; and the second population of unit dosage forms releases about 90% to about 10% of said at least one API.

In an aspect, the first population of unit dosage forms releases about 30% to about 40% of said at least one API; and the second population of unit dosage forms releases about 70% to about 60% of said at least one API.

In an aspect, the first population of unit dosage forms releases about 30% of said at least one API; and the second population of unit dosage forms releases about 70% of said at least one API.

In an aspect, the first population is delayed release (DR) and the second population is extended release (ER).

In an aspect, the ratio of DR:ER is selected from the group consisting of about 60:40, about 40:60, about 50:50, about 30:70 and about 20:80 of the total dose of at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

In an aspect, the first population of unit dosage forms releases most of said at least one API by a sudden burst or release of another specific amount of said at least one API in or around the duodenum but not past the hepatic flexure; and release of said at least one API of the second population of unit dosage forms is independent of gastrointestinal pH.

In an aspect, a ratio of the first population of unit dosage forms to the second population of unit dosage forms is about equipotent or has a potency ratio between about 0.5:100 to about 100:0.5.

In an aspect, the ratio is about 20 wt % to about 45 wt % of the first population of unit dosage forms to about 55 wt % to about 80 wt % of the second population of unit dosage forms.

In an aspect, the second population of unit dosage forms releases from about 60% to about 80% of said at least one API, and subsequently and/or concurrently, the first population releases about 20% to about 40% of said at least one API based on the wt % of at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

In an aspect, the second population of unit dosage forms is coated with at least one of ethylcellulose and acrylate copolymer and/or the first population of unit dosage forms is coated with at least one enteric coating.

In an aspect, the composition provides multiple site-specific delivery of said at least one API.

In an aspect, the composition provides multiple site-specific delivery in a rapid, delayed and controlled extended release manner in the gastrointestinal tract.

In an aspect, the multiple site-specific delivery is within the place in the upper small intestine where most of L-amino acid transporters reside, but not beyond the hepatic flexure.

In an aspect, the at least one unit dosage forms are selected such that drug release is via a three-phase trigger mechanism.

In an aspect, the second population of unit dosage forms releases from about 10% to about 60% of said at least one API in about one hour or less, which is the first trigger phase; followed by about 30% to about 70% of said at least one API of the second population, which is the second trigger phase; and subsequently and/or concurrently, the first population releases about 0% to about 50% when it encounters a pH of greater than about 5.0, which is the third trigger phase.

In an aspect, the at least one unit dosage forms comprises at least one of tablets, pills, caplets, capsules, sachets containing powder or granules, powder, granules, spheres, beads, pellets, liquid solutions or suspensions, emulsions, or capsules filled with the same, patches, and the like, and combinations thereof.

In an aspect, the at least one unit dosage forms comprises at least one of spheres, beads, tablets, granules and combinations thereof.

In an aspect, said at least one API comprises at least one of pregabalin, a base thereof, and a pharmaceutically acceptable salt thereof.

In an aspect, the composition further comprises at least one excipient.

In an aspect, said at least one excipient is selected from the group consisting of binders, surfactants, fillers, lubricants, glidants, disintegrating agents, colorants, wicking agents, extrusion aids, plasticizers, sustained release agents, anti-tacking agents, diluents, and combinations thereof.

In an aspect, said at least one excipient is present in an amount of from about 0.5% to about 95% by weight of said at least one unit dosage form.

In an aspect, at least one unit dosage form is made by extrusion spheronization or microencapsulation, drug layering on pharmaceutical spheres or compressed tablets.

In an aspect, the composition is in a housing suitable for oral application.

In an aspect, the housing is a capsule.

In an aspect, the capsule is a pulsed release capsule.

In an aspect, the composition has a dosage strength selected from the group consisting of about 37.5 mg, about 41.25 mg, about 75 mg, about 82.5 mg, about 150 mg, about 165 mg, about 300 mg, about 330 mg, about 450 mg, about 495 mg, about 600 mg, and about 660 mg.

In an aspect, on once daily dosing with meals, the following plasma concentrations ±30% are obtained, and time to maximum concentration of 5.0±40%, half life is 6.0±40% and rate at which said at least one API is removed in the body is 0.1±40%:

| Time (Hours) | Mean Plasma Test (ng/mL) | Coefficient of Variation Test (ng/mL) |
|---|---|---|
| 0 | 0 | Missing |
| 0.5 | 13 | 332 |
| 1.0 | 165 | 108 |
| 1.5 | 356 | 93 |
| 2.0 | 706 | 83 |
| 2.5 | 1209 | 46 |
| 3.0 | 1692 | 42 |
| 4.0 | 2093 | 20 |
| 5.0 | 2262 | 14 |
| 6.0 | 2197 | 13 |
| 7.0 | 2013 | 13 |
| 8.0 | 1837 | 16 |
| 9.0 | 1670 | 16 |

| Time (Hours) | Mean Plasma Test (ng/mL) | Coefficient of Variation Test (ng/mL) |
| --- | --- | --- |
| 10.0 | 1509 | 25 |
| 12.0 | 1189 | 30 |
| 13.0 | 1092 | 24 |
| 14.0 | 998 | 25 |
| 15.0 | 846 | 28 |
| 16.0 | 760 | 26 |
| 18.0 | 593 | 26 |
| 20.0 | 468 | 29 |
| 24.0 | 326 | 37 |
| 30.0 | 162 | 28 |
| 36.0 | 75 | 28 |

In an aspect, on once daily dosing without meals, the following plasma concentrations ±40%, and time to maximum concentration of 3.0±40%, half life is 7.2±40% and rate at which said at least one API is removed in the body is 0.1±40%:

| Time (Hours) | Mean Plasma Test (ng/mL) | Coefficient of Variation Test (ng/mL) |
| --- | --- | --- |
| 0.0 | 0 | Missing |
| 0.5 | 616 | 96 |
| 1.0 | 1590 | 48 |
| 1.5 | 1811 | 43 |
| 2.0 | 2100 | 32 |
| 2.5 | 2237 | 24 |
| 3.0 | 2504 | 21 |
| 4.0 | 2484 | 14 |
| 5.0 | 2216 | 23 |
| 6.0 | 1845 | 20 |
| 7.0 | 1700 | 26 |
| 8.0 | 1523 | 25 |
| 9.0 | 1348 | 28 |
| 10.0 | 1188 | 30 |
| 12.0 | 863 | 23 |
| 13.0 | 834 | 40 |
| 14.0 | 751 | 39 |
| 15.0 | 621 | 40 |
| 16.0 | 554 | 46 |
| 18.0 | 449 | 46 |
| 20.00 | 417 | 50 |
| 24.00 | 291 | 56 |
| 30.00 | 190 | 75 |
| 36.00 | 90 | 58 |

In an aspect, on once daily multiple dosing steady state without meals, the following plasma concentrations ±30%, and time to maximum concentration of 98.5±40%, minimum concentration is 91.0±40% and average concentration is 1088±40%:

| Time (Hours) | Mean Plasma Test (ng/mL) | Coefficient of Variation Test (ng/mL) |
| --- | --- | --- |
| 0.0 | 0.0 | Missing |
| 24.0 | 272 | 31 |
| 48.0 | 296 | 32 |
| 72.0 | 296 | 29 |
| 96.0 | 293 | 31 |
| 96.5 | 798 | 80 |
| 97.0 | 2070 | 51 |
| 97.5 | 2863 | 32 |
| 98.0 | 3189 | 24 |
| 98.5 | 3136 | 15 |
| 99.0 | 3053 | 14 |
| 100.0 | 2860 | 14 |
| 101.0 | 2489 | 18 |
| 102.0 | 2115 | 20 |
| 103.0 | 1755 | 24 |
| 104.0 | 1743 | 19 |
| 105.0 | 1594 | 17 |
| 106.0 | 1421 | 20 |
| 108.0 | 1110 | 22 |
| 109.0 | 995 | 22 |
| 110.0 | 870 | 25 |
| 111.0 | 780 | 23 |
| 112.0 | 682 | 25 |
| 114.0 | 508 | 26 |
| 116.0 | 410 | 30 |
| 120.0 | 282 | 30 |
| 126.0 | 143 | 37 |
| 132.0 | 91 | 52 |

In an aspect, on twice daily dosing without meals, the following plasma concentrations ±40% are obtained, and time to maximum concentration of 14.0±40%, half life is 7.1±40% and rate at which said at least one API is removed in the body is 0.1±40%:

| Time (Hours) | Mean Plasma Test (ng/mL) | Coefficient of Variation Test (ng/mL) |
| --- | --- | --- |
| 0.0 | 0.0 | Missing |
| 0.5 | 134 | 106 |
| 1.0 | 972 | 41 |
| 1.5 | 1220 | 34 |
| 2.0 | 1161 | 19 |
| 2.5 | 1182 | 18 |
| 3.0 | 1166 | 25 |
| 4.0 | 1145 | 26 |
| 5.0 | 1023 | 21 |
| 6.0 | 896 | 27 |
| 7.0 | 830 | 31 |
| 8.0 | 716 | 27 |
| 9.0 | 620 | 30 |
| 10.0 | 543 | 30 |
| 12.0 | 440 | 28 |
| 13.0 | 1134 | 49 |
| 14.0 | 1754 | 17 |
| 15.0 | 1653 | 20 |
| 16.0 | 1582 | 29 |
| 18.0 | 1240 | 24 |
| 20.0 | 991.5 | 30 |
| 24.0 | 713 | 29 |
| 30.0 | 417 | 35 |
| 36.0 | 217 | 35 |

In an aspect, on twice daily dosing with meal, the following plasma concentrations ±40% are obtained, and time to maximum concentration of 14.0±40%, half life is 5.9±40% and rate at which said at least one API is removed in the body is 0.1±40%:

| Time (Hours) | Mean Plasma Test (ng/mL) | Coefficient of Variation Test (ng/mL) |
| --- | --- | --- |
| 0.0 | 0 | Missing |
| 0.5 | 4 | 346 |
| 1.0 | 56 | 219 |
| 1.5 | 177 | 114 |
| 2.0 | 433 | 64 |
| 2.5 | 561 | 56 |
| 3.0 | 728 | 49 |

-continued

| Time (Hours) | Mean Plasma Test (ng/mL) | Coefficient of Variation Test (ng/mL) |
|---|---|---|
| 4.0 | 1155 | 43 |
| 5.0 | 1332 | 23 |
| 6.0 | 1170 | 18 |
| 7.0 | 1075 | 18 |
| 8.0 | 999 | 19 |
| 9.0 | 924 | 27 |
| 10.0 | 837 | 26 |
| 12.0 | 642 | 29 |
| 13.0 | 1450 | 31 |
| 14.0 | 1956 | 20 |
| 15.0 | 1918 | 22 |
| 16.0 | 1649 | 25 |
| 18.0 | 1370 | 23 |
| 20.0 | 1078 | 21 |
| 24.0 | 765 | 26 |
| 30.0 | 383 | 24 |
| 36.0 | 178 | 31 |

In an aspect, on once daily multiple dosing steady state without meals, the following plasma concentrations ±40%, and time to maximum concentration of 111.0±40%, minimum concentration is 274.5±40% and average concentration is 1041±40%:

| Time (Hours) | Mean Plasma Test (ng/mL) | Coefficient of Variation Test (ng/mL) |
|---|---|---|
| 0.0 | 0.0 | Missing |
| 24.0 | 756 | 18 |
| 48.0 | 887 | 26 |
| 72.0 | 889 | 22 |
| 96.0 | 836 | 22 |
| 96.5 | 936 | 16 |
| 97.0 | 1436 | 29 |
| 97.5 | 1636 | 25 |
| 98.0 | 1639 | 20 |
| 98.5 | 1703 | 18 |
| 99.0 | 1776 | 17 |
| 100.0 | 1647 | 21 |
| 101.0 | 1495 | 22 |
| 102.0 | 1338 | 22 |
| 103.0 | 1207 | 27 |
| 104.0 | 1077 | 24 |
| 105.0 | 945 | 26 |
| 106.0 | 842 | 24 |
| 108.0 | 636 | 25 |
| 109.0 | 1016 | 40 |
| 110.0 | 1784 | 27 |
| 111.0 | 2311 | 16 |
| 112.0 | 1948 | 15 |
| 114.0 | 1576 | 21 |
| 116.0 | 1206 | 19 |
| 120.0 | 844 | 18 |
| 126.0 | 417 | 24 |
| 132.0 | 274 | 28 |

In an aspect, the composition has the following dissolution time-percent release profile:

| Time [Min] | % Pregabalin released |
|---|---|
| 0 | 0 |
| 60 | 41 ± 30% |
| 70 | 73 ± 30% |
| 80 | 75 ± 25% |
| 90 | 77 ± 25% |
| 120 | 80 ± 25% |
| 150 | 83 ± 10% |
| 180 | 85 ± 10% |
| 240 | 89 ± 10% |
| 300 | 92 ± 10% |
| 360 | 94 ± 10% |

In an aspect, the composition has the following dissolution time-percent released profile:

| Time [Hr] | % Pregabalin released |
|---|---|
| 0 | 0 |
| 1 | 20 ± 30% |
| 2 | 43 ± 30% |
| 3 | 102 ± 10% |
| 4 | 105 ± 10% |
| 5 | 106.0 ± 10% |
| 6 | 106 ± 10% |
| 7 | 106 ± 10% |
| 8 | 107 ± 10% |

In an aspect, the composition has the following dissolution time-percent released profile:

| Time [Hr] | % Pregabalin released |
|---|---|
| 0 | 0 |
| 1 | 63 ± 30% |
| 2 | 82 ± 30% |
| 3 | 91 ± 10% |
| 4 | 97 ± 10% |
| 5 | 101 ± 10% |
| 6 | 102 ± 10% |
| 7 | 103 ± 10% |
| 8 | 104 ± 10% |
| 9 | 105 ± 10% |
| 10 | 105 ± 10% |
| 11 | 105 ± 10% |
| 12 | 107 ± 10% |

In an aspect, the composition has the following dissolution time-percent released profile:

| Time [Hr] | % Pregabalin released |
|---|---|
| 0 | 0 |
| 1 | 12 ± 30% |
| 2 | 41 ± 30% |
| 3 | 95 ± 15% |
| 4 | 98 ± 10% |

In an aspect, the composition has the following dissolution time-percent released profile:

| Time [Hr] | % Pregabalin released |
|---|---|
| 0 | 0 |
| 1 | 74 ± 20% |
| 2 | 89 ± 15% |
| 3 | 93 ± 15% |

-continued

| Time [Hr] | % Pregabalin released |
|---|---|
| 4 | 94 ± 15% |
| 5 | 95 ± 15% |

In an aspect, the composition has the following dissolution time-percent released profile:

| Time [Hr] | % Pregabalin released |
|---|---|
| 0 | 0 |
| 1 | 52 ± 30% |
| 2 | 80 ± 30% |
| 3 | 97 ± 25% |
| 4 | 97 ± 20% |
| 5 | 97 ± 10% |
| 6 | 98 ± 10% |

In an aspect, the size of said at least one unit dosage form is between about 0.01 mm to about 10 mm.

In accordance with an aspect, there is provided a method for management of neuropathic pain associated with at least one of diabetic peripheral neuropathy, management of post herpetic neuralgia, management of fibromyalgia, and as an adjunctive therapy for adult patients with partial onset seizures, the method comprising administering an effective amount of the composition described herein.

In accordance with an aspect, there is provided a method for treating a condition or disorder in a subject that is responsive to pregabalin, the method comprising administering an effective amount of the composition described herein.

In an aspect, the condition or disorder is selected from the group consisting of epilepsy, Huntington's chorea, cerebral ischemia, Parkinson's disease, tardive dyskinesia, spasticity, pain, physiological conditions associated with psychomotor stimulants, inflammation, gastrointestinal damage, alcoholism, insomnia, fibromyalgia, and various psychiatric disorders, including anxiety, depression, mania, and bipolar disorder.

In an aspect, the daily dose is in the range of 10-1200 mg of said at least one API.

In an aspect, the composition is orally administered.

In an aspect, the composition is suitable for dispersion in an aqueous liquid with neutral or slightly acidic pH-value before being orally administered or fed through a nasogastric tube.

In an aspect, the dosage strength is selected from the group consisting of about 37.5 mg, about 41.25 mg, about 75 mg, about 82.5 mg, about 150 mg, about 165 mg, about 300 mg, about 330 mg, about 450 mg, about 495 mg, about 600 mg and about 660 mg.

In accordance with an aspect, there is provided a use of an effective amount of the composition described herein for management of neuropathic pain associated with at least one of diabetic peripheral neuropathy, management of post herpetic neuralgia, management of fibromyalgia, and as an adjunctive therapy for adult patients with partial onset seizures.

In accordance with an aspect, there is provided a use of an effective amount of the composition described herein for treating a condition or disorder in a subject that is responsive to pregabalin.

In an aspect, the condition or disorder is selected from the group consisting of epilepsy, Huntington's chorea, cerebral ischemia, Parkinson's disease, tardive dyskinesia, spasticity, pain, physiological conditions associated with psychomotor stimulants, inflammation, gastrointestinal damage, alcoholism, insomnia, fibromyalgia, and various psychiatric disorders, including anxiety, depression, mania, and bipolar disorder.

In an aspect, the daily dose is in the range of 10-1200 mg of said at least one API.

In an aspect, the composition is orally administered.

In an aspect, the composition is suitable for dispersion in an aqueous liquid with neutral or slightly acidic pH-value before being orally administered or fed through a nasogastric tube.

In accordance with an aspect, there is provided an effective amount of the composition described herein for management of neuropathic pain associated with at least one of diabetic peripheral neuropathy, management of post herpetic neuralgia, management of fibromyalgia, and as an adjunctive therapy for adult patients with partial onset seizures.

In accordance with an aspect, there is provided an effective amount of the composition described herein for treating a condition or disorder in a subject that is responsive to pregabalin.

In an aspect,

In an aspect, the condition or disorder is selected from the group consisting of epilepsy, Huntington's chorea, cerebral ischemia, Parkinson's disease, tardive dyskinesia, spasticity, pain, physiological conditions associated with psychomotor stimulants, inflammation, gastrointestinal damage, alcoholism, insomnia, fibromyalgia, and various psychiatric disorders, including anxiety, depression, mania, and bipolar disorder.

In an aspect, the daily dose is in the range of 10-1200 mg of said at least one API.

In an aspect, the composition is orally administered.

In an aspect, the composition is suitable for dispersion in an aqueous liquid with neutral or slightly acidic pH-value before being orally administered or fed through a nasogastric tube.

In an aspect, the dosage strength is selected from the group consisting of about 37.5 mg, about 41.25 mg, about 75 mg, about 82.5 mg, about 150 mg, about 165 mg, about 300 mg, about 330 mg, about 450 mg, about 495 mg, about 600 mg and about 660 mg.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

DETAILED DESCRIPTION OF CERTAIN EMBODIMENTS

Figure 1:
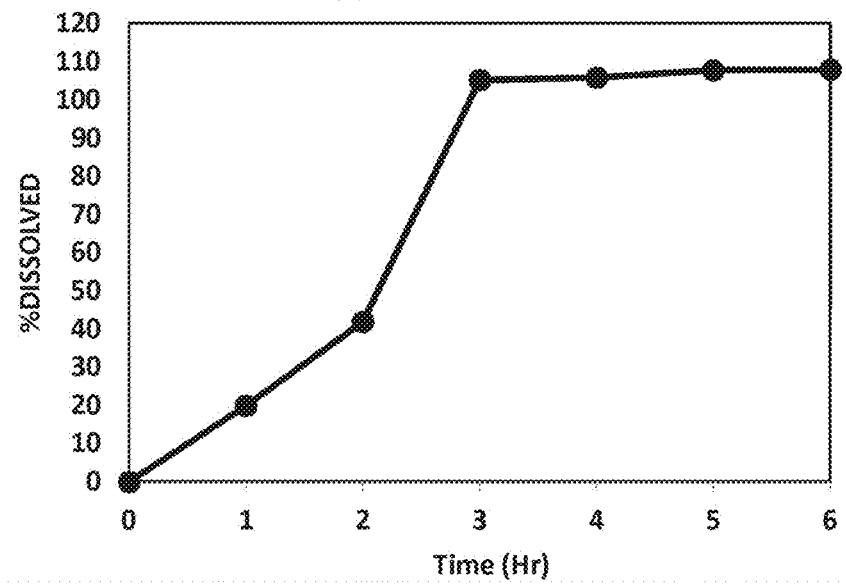
FIG. 1 shows dissolution of 150 mg of pregabalin pH-dependent beads from Example 1, at 37° C., 100 rpm in 0.06N HCl for about 2 hours followed by pH 6.0 buffer for about 4 hours.

As has been explained above, pregabalin is a known drug for use in treatment of a number of different disorders. However, it has been very difficult to design pregabalin-containing formulations for once-a-day administration, which can show bioequivalence and superiority in exposure to a twice-a-day administration, using conventional technologies for sustained release formations. Pregabalin absorption increases from small intestine towards large intestine, and becomes poor beyond the hepatic flexure. Conventional tablets are transferred to the hepatic flexure in about six hours or less, on average, thereafter losing efficiency due to poor absorption in the remaining parts of the intestine. Any drug release from a conventional extended release (ER) dosage form beyond six hours would thus be wasted because the dosage form has traveled beyond the hepatic flexure.

It has also been difficult to design efficient pregabalin-containing formulations for once-a-day administration, especially using swellable, flotation or gastroretentive systems because of inability to minimize the individual variations inherent in these devices on the one hand and devices transiting past the main absorption window for pregabalin in the GI tract before or without the release of most of its pregabalin content, due to unpredictability of GI transit times and motilities.

In aspects, the pregabalin-containing formulations described herein are suitable for once-a-day administration, and take into account the symptomatology and chronobiology of, for example, fibromyalgia and other related conditions.

It is now a well-accepted fact, that administering conventional immediate release formulations many times a day leads to substantial fluctuations in the plasma concentration of a drug. Consequently, to achieve relatively constant plasma concentration throughout the day, once daily administration is desirable. The convenience of once a day dosing improves patient compliance, especially for elderly patients and for patients on multiple medications, as it is not easy for everyone to remember to take the correct dose at the same time each day. Once per day dosing may also lessen or prevent potentially undesirable dose-related effects by reducing peak blood levels, which can be particularly true for pregabalin. Pregabalin is conventionally dosed two- or three-times daily. The conversion of pregabalin administered twice a day into a form for once-a-day administration, as described herein, may improve patients' drug compliance; potentially reduce any side effects originated from maximum blood concentration exceeding the desired effective blood concentration and/or sudden increase of blood concentration; and increase the maintenance time of effective blood concentration, thereby increasing pharmacological effects.

However, once daily dosing of pregabalin, and the design of a pregabalin-containing formulation for once a day administration, and particularly one that can give higher blood plasma exposure in, for example, about the first twelve hours of administration and also lessen or prevent potentially undesirable dose-related effects, by reducing peak blood levels (CMAX) and also increase drug efficacy by increasing minimum plasma concentrations (CMIN) in the presence of an evening meal, presents numerous challenges and has proven elusive as pregabalin is not absorbed uniformly in the GI tract, because pregabalin is absorbed through L-amino acid transport system. This is further exacerbated by the fact that the rate of pregabalin absorption is decreased when given with food.

Furthermore, because the absorption of pregabalin takes place in the upper small intestine where most of L-amino acid transporters reside, and is poorly absorbed beyond the hepatic flexure, an average absorption window thereof is less than 6 hours (Su T-Z, Feng M R, Weber M L: Mediation of highly concentrative uptake of pregabalin by L-type amino acid transport in Chinese hamster ovary and Caco-2 cells. J Pharmacol Exp Ther 2005, 313:1406-1415), providing a once-a-day formulation which is bioequivalent to a twice-a-day immediate release formulation in terms of peak plasma exposure and total exposure poses several challenges.

Furthermore, pregabalin is a γ-amino acid which under the influence of ambient and physical storage conditions may undergo intramolecular cyclization to form a lactam, 4-isobutyl-pyrrolidin-2-one. See, e.g., WO 99/10186 and WO 99/59573, both to A. Aomatsu. Stability-related problems do occur and are not desirable for the formulation.

In aspects, described herein is a once daily or twice daily pregabalin controlled extended release formulation that may provide chemical stability and more precise control of the release of pregabalin within the place in the upper small intestine where most of L-amino acid transporters reside, but, typically, not beyond the hepatic flexure.

Also described herein in aspects is a once daily or twice daily pregabalin controlled extended release formulation that takes into consideration the symptomatology and chronobiology of, for example, fibromyalgia and may be bioequivalent and give higher exposure than immediate release pregabalin given twice a day with a meal. In aspects, described herein are treatments of fibromyalgia syndrome that take into consideration the symptomatology and chronobiology of fibromyalgia and formulations that may improve patient compliance and efficacy in the treatment of pain, sleep, fatigue and other comorbidities including depression and reduce side effect profiles encountered by fibromyalgia patients.

Definitions:

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Treating" generally refers to an approach for obtaining beneficial or desired clinical results. For example, "treating," in aspects, refers to ameliorating, reversing, alleviating, inhibiting the progress of, or preventing a disorder or condition in a subject, or to preventing one or more symptoms of such disorder or condition in the subject.

"Treatment" refers to the act of "treating" as defined immediately above.

"ER" refers to extended release and "DR" refers to delayed release.

"Drug," "drug substance," "active pharmaceutical ingredient," and the like, refer to a compound (e.g., pregabalin) that may be used for treating a subject in need of treatment.

"Therapeutically effective amount" means a quantity sufficient, when administered to a subject, including a mammal, for example a human, to achieve a desired result. Effective amounts of the compounds described herein may vary according to factors such as the disease state, age, sex, and weight of the subject. Dosage or treatment regimes may be adjusted to provide the optimum therapeutic response, as is understood by a skilled person. For example, the quantity of the drug that may be used for treating a subject may be generally in the range of about 0.001 to about 100 mg/kg/day for an adult, and is often in the range of about 0.1 to about 50 mg/kg/day for an adult. For an adult human, a typical daily dose of a drug is in the range of about 1 mg to about 1000 mg. For pregabalin, the daily dose for an adult human may be in the range of about 20 mg to about 1800 mg and is often in the range of about 50 mg to about 900 mg.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question.

"Inert" substances refer to those substances that may influence the bioavailability of the drug, but are otherwise pharmaceutically inactive.

"Excipient" or "adjuvant" refers to any inert substance, used, for example, as a carrier or vehicle for delivery of an API to a subject or added to a pharmaceutical composition to improve its handling or storage properties or to permit or facilitate formation of a dose unit of the composition The term "hydrate" refers to a solvate comprising pregabalin and a stoichiometric or non stoichiometric amount of water.

The term "solvate" refers to a molecular complex comprising pregabalin and a stoichiometric or non-stoichiometric amount of one or more solvent molecules (e.g., EtOH).

The term "polymorph" refers to the property of some molecules and molecular complexes to assume more than one crystalline or amorphous form in the solid state.

"Formulation", "pharmaceutical formulation", "composition" and "pharmaceutical composition" may be used interchangeably.

A "unit dosage form", "drug product", "pharmaceutical dosage form," "dosage form," and "final dosage form" and the like, refer to a pharmaceutical composition, which, generally, may be in the form of tablets, pills, caplets, capsules, sachets containing powder or granules, powder, granules, spheres, beads, pellets, liquid solutions or suspensions, emulsions, or capsules filled with the same, patches, and the like, and combinations thereof.

A "population" of "unit dosage form", "drug product," "pharmaceutical dosage form," "dosage form," and "final dosage form" refers to at least two of a "unit dosage form", "drug product," "pharmaceutical dosage form," "dosage form," and "final dosage form". It is understood that "at least two" refers to two or more and any incremental range therebetween. The population of dosage forms may vary depending on the application.

A test dosage form is "bioequivalent" to a reference dosage form if the about 90% confidence interval estimate for the ratio of the mean value of the total exposure from treatment with the test dosage form to the mean value of the total exposure from treatment with the reference dosage form lies within the range of about 80% to about 125%. Here, the ratio is expressed as a percentage (100%×test/reference) and the about 90% confidence interval is expressed as a percentage of the reference mean. For single-dose studies, the total exposure is the area under the plasma concentration-time curve from time zero (time of dosing) to time infinity; for steady-state studies, the total exposure is the area under the plasma concentration-time curve over the dosing interval. See, U.S. Department of Health and Human Services, Food and Drug Administration, Center for Drug Evaluation and Research, Guidance for Industry, Bioavailability and Bioequivalence Studies for Orally Administered Drug Products—General Considerations (Rev. 1, March 2003).

"Active ingredient," "active agent," or "active substance" means any compound which has biological, chemical, or physiological utility including, without limitation, active pharmaceutical ingredient, drug, naturally occurring compound, nucleic acid compound, peptide compound, biologics, nutraceutical, agricultural or nutritional ingredient or synthetic drug, including addictive substances such as opioid agonists or narcotic analgesics, hypnotics, tranquilizers, stimulants and antidepressants.

The formulations/compositions herein may also contain one or more other active ingredients. These include, amongst others and for example, and without being limited thereto, antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, and diclofenac sodium. opioid antagonists (such as naloxone), phenacetin, caffeine, acetaminophen, antihistamines, homatropine methylbromide, phenyltoloxamine citrate, barbiturates, or the like, or multiple combinations thereof.

Formulations herein may also comprise narcotic analgesics in combination with non-narcotic analgesics, antitussive preparations which contain narcotic or narcotic-like cough suppressants such as codeine, dihydrocodeinone, pholcodeine, and the like. Other products comprising a narcotic or narcotic-like composition for use as an antispasmodic in the gastro-intestinal tract, such as Camphorated Opium Tincture, U.S.P., Opium Tincture, U.S.P., Opium extract, N.F., and the like may also be included.

Any desired amounts of the active substance may be used in the formulation described herein.

The term "enteric coat" refers to a coat that is stable at the highly acidic pH found in the stomach, but breaks down at a less acidic (relatively more basic) pH. For example, enteric coats will not dissolve in the stomach but they will in the basic pH environment present in the small intestine. Materials used for enteric coatings include polymers such as fatty acids, waxes, shellac, plastics, and plant fibers.

The term "Eudragit RL" is referred to as a pH-independent polymer and may be any poly(ethyl acrylate-co-methyl methacrylate-co-trimethylammonioethyl methacrylate chloride. Examples include, but are not limited to, Eudragit RL™, Eudragit RL 100™, Eudragit™ RL PO, Eudragit™ RL 30 D, and Eudragit™ RL 12,5.

The terms "Eudragit NE", "Eudragit RS" and "Eudragit NM" are referred to as pH-independent polymers and may be any neutral copolymer based on ethyl acrylate and methyl methacrylate. Examples include, but are not limited to, Eudragit™ NE 30 D, Eudragit™ NE 40 D, and Eudragit™ NM 30 D, Eudragit™ RS 100, Eudragit™ RS PO, Eudragit™ RS 30 D, and Eudragit™ RS 12,5.

The terms "Eudragit L" and "Eudragit S" are referred to as enteric polymers and may be any anionic copolymers based on methacrylic acid and methyl methacrylate. Examples include Eudragit™ L 100, Eudragit™ L 12,5, Eudragit™ S 12,5 and Eudragit™ S 100. The ratio of the free carboxyl groups to the ester groups is approx. 1:1 in Eudragit™ L 100 and approx. 1:2 in Eudragit™ S 100.

The term "coat" may be variously characterized as a coating, layer, membrane, film, shell, capsule, or the like, and may partially, substantially or completely surround or envelope. For example, the "coat" may cover portions of the surface to which it is applied; e.g. as a partial layer, partial coating, partial membrane, partial film, or partial shell; it may, for example, be in the form of half spheres that cover the surface.

The term "controlled release" may be variously characterized by "sustained release", "sustained action", "extended release", "modified release", "pulsed release", "delayed release", "targeted release", "site-specific release", and "timed release", which are used interchangeably herein and are herein defined as the time of release, the extent of release, the rate of release, the site of release and/or release of an active ingredient from a formulation at such a rate that when a dose of the active ingredient is administered in the sustained release, extended release, pulsed release, timed release, delayed release or controlled-release formulation, concentrations (levels) of the active ingredient are maintained within a desired range but below toxic levels over a selected period of time. In the case of in vivo administration, concentrations (levels) of the active ingredient could be measured in blood or plasma, for example. When administered in vivo the sustained release, extended release, pulsed release, timed release, delayed release or controlled-release formulation allows for a timely onset of action and useful plasma concentration of an active ingredient to be maintained for longer than in the case of immediate-release forms.

The term "inhibit" refers to partially, substantially, or completely slowing, hindering, reducing, delaying or preventing. The terms inhibit, reduced, prevented, delayed, and slowed may be used interchangeably.

The term "wicking agent", is defined as any material with the ability to draw water into the network of a delivery dosage form. For example, by so doing, a wicking agent provides enhanced flow channels for the pharmaceutical agent, which has been made predominantly into its solubilized form.

Controlled Extended Release Pharmaceutical Compositions and Methods for Making Same In general, a controlled extended release composition comprises at least one unit dosage form having at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof. Such a composition may be a once- or twice-a-day controlled extended release pharmaceutical composition. The composition, which on oral administration under fasting conditions, and/or following, during or after a meal, may provide higher exposure to pregabalin, within a predetermined period of time (e.g. about twelve hours) of administration compared to commercial immediate release preparations taken twice or thrice a day, such as LYRICA™ (pregabalin) immediate release composition.

In another embodiment, the at least one unit dosage form comprises at least two unit dosage forms. Such a composition may be a once- or twice-a-day controlled extended release pharmaceutical composition. The composition, which on oral administration under fasting conditions, and/or following, during or after a meal, may provide higher exposure to pregabalin, within a predetermined period of time (e.g. about twelve hours) of administration compared to commercial immediate release preparations taken twice or thrice a day.

Each unit dosage form may have predetermined distinct timed drug release characteristics and/or dissolution/rate profiles. In aspect, "distinct" means that certain drug release characteristics and/or dissolution/rate profiles are separate and independent of one another. The unit dosage forms may be chosen such that drug release is via a multiple-phase trigger mechanism. For example, a three-phase trigger mechanism utilizing pH-dependent and pH-independent unit dosage forms. The composition may provide multiple site-specific delivery of at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof. For example, the composition may provide multiple site-specific delivery in a rapid, delayed and controlled extended release manner in the GI tract (i.e., within the place in the upper small intestine where most of L-amino acid transporters reside, but not in substantive amounts beyond the hepatic flexure), resulting in high pregabalin exposure as seen in plasma concentration time curves in pharmacokinetic studies.

In a further embodiment, the at least one unit dosage form comprises at least one population of unit dosage forms. Each population of unit dosage forms may have distinct timed drug release characteristics and/or dissolution/rate profiles. Each population may be intermixed (e.g. adhered to, adjacent to, etc.) and/or physically separate from (e.g. by a barrier) another population of unit dosage forms such that each population has independent and separately distinct pharmacokinetics and/or pharmacodynamics. Portions of populations may be intermixed and other portions of populations may be physically separate from one another.

In another embodiment, the at least one unit dosage form comprises (i) a unit dosage form and (ii) at least one population of unit dosage forms. The unit dosage form of (i) and each population of unit dosage forms of (ii) may have distinct timed drug release characteristics and/or dissolution/rate profiles. Each population of (ii) may be intermixed (e.g. adhered to, adjacent to, etc.) and/or physically separate from (e.g. by a barrier) another population of unit dosage forms and/or the unit dosage form of (i).

In a further embodiment, the at least one unit dosage form comprises (i) at least two unit dosage forms, wherein one or more unit dosage forms have a distinct timed drug release characteristics and/or dissolution/rate profile from one or more other unit dosage forms; and (ii) at least one population of unit dosage forms. The at least two unit dosage forms of (i) and each population of unit dosage forms of (ii) may have distinct timed drug release characteristics and/or dissolution/rate profiles. Each population of (ii) may be intermixed (e.g. adhered to, adjacent to, etc.) or physically separate from (e.g. by a barrier) another population of unit dosage forms and/or the at least two unit dosage forms of (i).

In more specific embodiments, the at least one unit dosage form comprises at least two populations of unit dosage forms. Each population of unit dosage forms having distinct timed drug release characteristics and/or dissolution/rate profiles. Each population may be adhered to, juxtaposed to and/or physically separate from (e.g. by a barrier) another population of unit dosage forms.

The unit dosage forms described herein may be tablets, pills, caplets, capsules, sachets containing powder or granules, powder, granules, spheres, beads, pellets, liquid solutions or suspensions, emulsions, or capsules filled with the same, patches, and the like, and combinations thereof. Typically, the unit dosage forms are at least one of spheres, beads, tablets, and granules, that is useful for once daily or twice daily oral dosing.

At least two populations of said at least two populations of unit dosage forms comprise at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

For example, a controlled extended release pharmaceutical composition comprises at least two populations of unit dosage forms. Each unit dosage form comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof. At least one population of the at least two populations of unit dosage forms are encapsulated or coated. The unit dosage forms of the at least two populations of unit dosage forms may be tablets, pills, caplets, capsules, sachets containing powder or granules, powder, granules, spheres, beads, pellets, liquid solutions or suspensions, emulsions, or capsules filled with the same, patches, and the like, and combinations thereof. Typically, the unit dosage forms are at least one of spheres, beads, tablets, and granules, that is useful for once daily or twice daily oral dosing. At least one population of unit dosage forms is coated with a pH-dependent coat(s) from which drug release depends on pH of the surrounding environment while at least one of the other populations is coated with a pH-independent coat(s) from which drug release is independent of pH of the surrounding environment. In an example of the composition, a ratio is such that (i) one population of unit dosage forms coated with the pH-dependent coat(s) releases about 10% to about 90% of the pregabalin (and/or other forms of pregablin described herein) and (ii) the other population of unit dosage forms with the pH-independent coat(s) releases about 90% to about 10% of the pregabalin (and/or other forms of pregabalin described herein). A further example of a ratio is such that (i) one population of unit dosage forms coated with the pH-dependent coat(s) releases about 30% to about 40% of the pregabalin (and/or other forms of pregablin described herein) and (ii) the other population of unit dosage forms with the pH-independent coat(s) releases about 70% to about 60% of the pregabalin (and/or other forms of pregablin described herein).

In one embodiment, the at least one unit dosage form comprises two populations of unit dosage forms. Each population of unit dosage forms having distinct timed drug release characteristics and/or dissolution/rate profiles. Each population may be adhered to, juxtaposed to and/or physically separate from (e.g. by a barrier) another population of unit dosage forms. Each population comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

The ratio of the two distinct populations of unit dosage forms may be such that it provides timed drug release at specific times and in specific regions of the GI site. For example, administration of a specific/calculated amount of pregabalin is primed to be released by one pH-independent population of unit dosage forms (for example, instantaneously or in less than about two hours) followed by release of the remainder at pre-determined rates by the same pH-independent population of unit dosage forms in the stomach and upper small intestine but, typically, not past the hepatic flexure. Pregabalin release by this population is independent of gastrointestinal pH. The other pregabalin pH-dependent population of unit dosage forms releases all of its pregabalin by a sudden burst or release of another specific amount of pregabalin in or around the duodenum but, typically, not past the hepatic flexure. Complete pregabalin release by this population is dependent on gastrointestinal pH, being designed to be triggered by pH greater than about 5.0.

In another embodiment, the controlled extended release pharmaceutical composition of pregabalin comprises two distinct populations of unit dosage forms of pregabalin presented as one or a combination of beads, pellets, tablets and granules provided in a capsule. The composition comprises (i) a first population of unit dosage forms having at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein complete drug release is at a certain pH (e.g. pH greater than about 5.0); and (ii) a second population of unit dosage forms having at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate, wherein drug release is stepwise and pH-independent.

In another embodiment of the the controlled extended release pharmaceutical composition of pregabalin comprising two distinct populations of unit dosage forms, the composition comprises (i) a first pH-dependent population of unit dosage forms having at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the unit dosage forms are encapsulated or coated by polymeric or pharmaceutically acceptable materials that can act as pH-dependent agent(s) (e.g. enteric coating material) and (ii) a second pH-independent population of unit dosage forms having at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the unit dosage forms are encapsulated or coated by polymeric or pharmaceutically acceptable materials that can act as pH-independent agent(s) (e.g. ethylcellulose and/or acrylate copolymer).

The unit dosage form(s) can be made by layering the API on cores (e.g. sugar or cellulose), which may be made by extrusion spheronization or by mixing the pregabalin with a selected excipient and compressing the mixture into tablets.

In the case of powder solution layering techniques for producing unit dosage form(s) (e.g., pregabalin immediate release cores), the size of the cores may vary, for example, between about 0.1 and about 4 mm. The cores layered with pregabalin API (e.g. at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof) may be produced either by powder or solution/suspension layering using for instance granulating or spray coating/layering equipment. Alternatively, cores (e.g. pellets) may be produced by extrusion/spheronization, balling or compression utilizing different process equipment as is understood by one of skill in the art. The size of the formulated cores is approximately between about 0.001 mm and about 4 mm and typically, between about 0.1 mm and about 2 mm. The manufactured cores may then be coated with the pharmaceutical active substance. Thus the size of the prepared unit dosage form(s) (e.g. beads, pellets, tablets, granules etc.) may vary, for example, between about 0.01 to about 25 mm and any size as desired therebetween.

The various unit dosage form(s) may be provided within a suitable capsule material as is understood by one of skill in the art. Suitable capsule materials may include for example, but are not limited to, gelatin, cellulose ethers, cellulose, biodegradable non-toxic materials and combinations thereof. One of skill in the art would readily understand the process and manner of providing the oral composition within a capsule.

The unit dosage forms described herein may be formulated using any known technique such as, for example, dry granulation, direct compression, wet granulation, melt granulation and extrusion-spheronization. For example, the unit dosage forms may include a core material, for example, made from extrusion-spheronization, drug solution layering or fluid bed coating sugar spheres or microcrystalline cellulose spheres of about 0.001 mm to about 5 mm. Alternatively, the unit dosage forms may be provided as a tablet of about 0.1 mm to about 20 mm. The unit dosage forms may then be provided within a suitable housing such as hard gelatin or hydroxypropylmethyl cellulose capsule suitable for oral administration by various mechanisms as further described herein.

The compositions described herein may be in the form of a non-gas driven, non-floating, non-hydrogelling, non-swelling and/or non-matrix system. The compositions may be made by (1) preparing an immediate release core containing unit dosage form of pregabalin by one of the following methods: extrusion-spheronization, powder solution layering, microencapsulation, fluid bed coating, hot melt extrusion or tableting techniques; (2) applying a pH-dependent coat to immediate release cores to form one population of pregabalin delayed release spheres; (3) applying a pH-independent coat to immediate release cores to form one population of pregabalin extended release spheres and (4) encapsulating a predetermined proportion of the pH-dependent population and a predetermined proportion of the pH-independent population in a housing such as a capsule (e.g. hard gelatin capsule).

In another embodiment, the controlled extended release pharmaceutical composition has a ratio of the first pH-dependent population of unit dosage forms to the second pH-independent population of unit dosage forms that is about equipotent or has a potency ratio between about 0.5:100 to about 100:0.5. The populations may be presented as one or a combination of beads, pellets, tablets and granules provided in a capsule. The two populations may be combined in the ratio of about 20 wt % to about 45 wt % delayed release (DR) to about 55 wt % to about 80 wt % extended release (ER) based on wt % of pregabalin. The populations may be encapsulated in one unit dosage form such as a capsule. For example, in Example 1 shown below, the two populations are combined in the ratio of about 30:70 DR:ER and are placed in a capsule (e.g., if ER potency is about 69% and DR potency is about 67% then pregabalin controlled extended release capsules 165 mg will contain about 74 mg of DR and about 166 mg of ER. Thus, about 49.5 mg of pregabalin is contributed by DR population, while about 115.5 mg of pregabalin is contributed by ER population). In another example, the two populations are combined in the ratio of about 60:40 DR:ER and are placed in a capsule (e.g., if ER potency is about 50% and DR potency is about 50% then pregabalin controlled extended release capsules 150 mg will contain about 180 mg of DR and about 120 mg of ER. Thus, about 90 mg of pregabalin is contributed by DR population, while about 60 mg of pregabalin is contributed by ER population).

Another embodiment relates to a capsule containing multiple populations of pregabalin spheres, consisting of two distinct populations (e.g., an extended release (ER) population containing about 80% of total pregabalin (or other forms) and a delayed release (DR) population containing about 20% of total pregabalin (or other forms) in the dosage form) acting in unison to provide a three phased trigger mechanism for the precise release of pregabalin in the appropriate area in the GI tract. On oral administration, drug release follows a step wise release of pregabalin (or other forms), wherein, for example, the extended release population releases from about 10% to about 60% of pregabalin (or other forms) in about one hour or primed to be released instantaneously (this constitutes the first trigger/phase and initial contribution by the extended release population) followed by controlled release of the remaining about 30% to about 70% (this constitute the second trigger/phase and final contribution by the extended release population). Subsequently and/or concurrently the delayed release population instantaneously releases the remaining pregabalin (or other forms) of about 0% to about 50% (this constitutes the third trigger/phase and the contribution by the delayed release population) when it encounters a pH of greater than 5.0. The percentages chosen will add up to 100% release of pregabalin (or other forms). All of these activities typically take place in the stomach region with slight spill over into the duodenum.

In other embodiments, the second population of unit dosage forms releases from about 10% to about 60% of said at least one API in about one hour or less, which is the first trigger phase; followed by about 30% to about 70% of said at least one API of the second population, which is the second trigger phase; and subsequently and/or concurrently, the first population releases about 0% to about 50% when it encounters a pH of greater than about 5.0, which is the third trigger phase.

In other embodiments, the second population of unit dosage forms releases from about 20% to about 60% of said at least one API in about one hour or less, which is the first trigger phase; followed by about 40% to about 60% of said at least one API of the second population, which is the second trigger phase; and subsequently and/or concurrently, the first population releases about 30% when it encounters a pH of greater than about 5.0, which is the third trigger phase.

The active pharmaceutical ingredient (API) of the compositions described herein includes, typically, at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof. More typically, the API includes at least one of pregabalin, a base thereof, and a pharmaceutically acceptable salt thereof. Even more typically, the API includes at least one of pregabalin and a base thereof. When referring to "pregabalin content", it is understood to cover at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof.

The APIs may be in the core of the unit dosage form(s) and/or in the coating(s).

In embodiments, the unit dosage form(s) (e.g. capsule, tablet, pellet, bead etc.) of pregabalin API comprises about 2% to about 95% by weight pregabalin based on the weight of the unit dosage form(s).

Examples of pregabalin controlled extended release formulations may have the following dosage strength of from about 10 mg to about 1200 mg or specifically, about 37.5 mg, about 41.25 mg, about 75 mg, about 82.5 mg, about 150 mg, about 165 mg, about 300 mg, about 330 mg, about 450 mg, about 495 mg, about 600 mg and about 660 mg. The formulations typically contain 20 to 1000 mg pregabalin as a base. The formulations/compositions embodiments described herein may further comprise other active pharmaceutical ingredients (API). Other APIs that may be combined with pregabalin include, but are not limited to, anti-depressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, and diclofenac sodium. The other APIs may be in the core of the unit dosage form(s) and/or in the coating(s) of the unit dosage form(s) with pregabalin as the API. Therefore, the other APIs may be present in combination with the pregabalin API and/or as a separate unit dosage form(s). For example, the other API may be in the same unit dosage form(s) with the pregabalin API or separately as a different at least one unit dosage form and/or at least one population of unit dosage forms. The different at least one unit dosage form and/or at least one population of unit dosage forms may be an immediate release or controlled release such as spheres, beads, pellets, tablets or other pharmaceutically suitable dosage forms.

When the coat(s) are applied to the unit dosage form(s), it may constitute a variable thickness. Any suitable thickness may be used. The maximum thickness of which is normally only limited by processing conditions.

The pH-dependent coating material may be dispersed or dissolved in either water or in suitable organic solvents. One or more enteric coating polymers may be used. Typical examples include one or more, separately or in combination, of the following: solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac, zein or other suitable enteric coating polymer(s). Specific enteric polymers that may be used are Eudragit L™ and/or Eudragit S™ which preferentially dissolve in the more alkaline pH of the intestine, or polymers which dissolve slowly, e.g. a predetermined rate in the digestive tract, such as Eudragit RL™, e.g. Eudragit RL 100™, and/or Eudragit RS™ e.g. Eudragit R100™, and/or blends of such Eudragit™ polymers.

The pH-dependent coatings may contain pharmaceutically acceptable plasticizers to obtain the desired mechanical properties, such as flexibility and hardness of the pH-dependent coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for each pH-dependent coating layer formula, in relation to selected pH-dependent coating layer polymer(s), selected plasticizer(s) and the applied amount of said polymer(s), in such a way that the release properties are adjusted so that the acid resistance of the pellets covered with enteric pH-dependent coating, layer(s) is optimal. The amount of plasticizer is usually above about 10% by weight of the pH-dependent coating layer polymer(s), about 15 to about 50%, or about 20 to about 50%. Additives such as dispersants, colorants, pigments, polymers e.g. poly(ethylacrylate, methylmethacrylate), anti-tacking and anti-foaming agents may also be included into the pH-dependent coating(s). Other compounds may be added to increase film thickness and to decrease diffusion of acidic gastric juices into the pH-dependent coated populations.

The pH-dependent coated populations of pregabalin, typically, demonstrate a measure of acid resistance defined as the amount of pregabalin released after being exposed to 0.1N HCl (aq). The test may be carried out in the following manner. The pH-dependent coated beads, tablets or pellets are exposed to 0.1N HCl at a temperature of 37° C. in a USP dissolution apparatus for about two hours and do not disintegrate and release more than about 40%±25 of the pregabalin. After about two hours, the pH-dependent coating layered beads, pellets tablets or granules are exposed to phosphate buffer (pH 6.0) and greater than about 70% of the pregabalin is released in about one hour following such exposure.

The pH-dependent coat applied to unit dosage form(s) may be composed of about 0.001 to about 90% of a pH-dependent polymer. Examples of the pH-dependent coat applied to the unit dosage form(s) being composed of about 0.001 to about 90% of cellulose esters, polyvinyl acetate phthalate, methacrylic acid copolymer type A, methacrylic acid copolymer type B, methacrylic acid copolymer type C, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, Chitosan, Shellac, Zein, cellulose acetate trimellitate or any mixture thereof. The coat displays pH-dependent solubility such that it is insoluble in acid medium but soluble in alkaline medium.

The pH-dependent coatings may contain pharmaceutically acceptable plasticizers to obtain the desired mechanical properties, such as flexibility and hardness of the pH-dependent coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for each pH-dependent coating layer formula, in relation to selected pH-dependent coating layer polymer(s), selected plasticizer(s) and the applied amount of said polymer(s), in such a way that the release properties are adjusted so that the acid resistance of the pregabalin cores covered with selected pH-dependent coating, layer(s) is optimal. The amount of plasticizer is typically above about 10% by weight of the selected pH-dependent coating layer polymer(s), about 15 to about 50%, or about 20 to about 50%. Additives such as dispersants, disintegrants, colorants, pigments, polymers e.g. cellulose ethers, poly(ethylacrylat, methylmethacrylate), anti-tacking and anti-foaming agents may also be included in the selected pH-dependent coating layer(s). Other compounds may be added to increase film thickness and to decrease diffusion of acidic gastric juices into the selected pH-dependent coated populations.

The pH-independent coat applied to unit dosage form(s) may be composed of about 0.001 to about 90% of a pH-independent polymer. Examples of the pH-independent coat applied to the unit dosage form(s) may be composed of about 0.001 to about 90% of ethylcellulose, ammonium methacrylate copolymer, ethyl acrylate and methyl methacrylate copolymer, or any mixture thereof. The coat displays pH-independent drug release characteristics. The coat(s) may comprise one or more of cellulose ethers, oils, plasticizers, anti-tacking agents, disintegrants, colorants, pregabalin and its derivatives.

For the pH-dependent or pH-independent coats of the orally administered formulations, polymers that are known to be orally ingestible can be used. Other known polymers useful for enteral delivery include polymer materials, which preferentially dissolve or disintegrate at different points in the digestive tract. Such polymers include, for example, the known acrylic and/or methacrylic acid-based polymers, which are soluble in intestinal fluids, e.g. the Eudragit™ series of commercially available polymers.

With respect to the unit dosage form(s), including population(s) of unit dosage forms, described herein, one or more of the unit dosage forms, including population(s) of unit dosage forms, may further be provided with one or more over-coating layers, for example, colorants etc., or dusted with anti-static materials such as silicone dioxide and talc.

The compositions described herein may further include at least one excipient. The amount of excipient in unit dosage form(s) may comprise about 0.5% to about 95% wt/wt of the unit dosage form(s) in which it is used. The unit dosage form(s) may be, for example, beads, pellets, tablets or granules. The excipients may be included into the core, coats or simply blended in after coating prior to encapsulation.

The excipient(s) may be selected from the group consisting of binders, surfactants, fillers, lubricants, glidants, disintegrating agents, colorants, pigments, wicking agents, extrusion aids, plasticizers, sustained release agents, antistatic agents, anti-tacking agents, diluents, other pharmaceutically acceptable ingredients and combinations thereof. Excipients are used to obtain preferred handling and processing properties and suitable concentrations of the pharmaceutical active substance. Some examples of excipients that may be present are, a variety of cellulose derivatives such as hydroxypropyl methylcellulose, hydroxypropyl cellulose and carboxymethyl-cellulose sodium, polyvinyl pyrrolidone, sugars, starches, carrageenan, magnesium stearate, titanium dioxide, talc and other pharmaceutically acceptable substances with wicking properties.

Suitable surfactants that may be present are found in the groups of pharmaceutically acceptable non-ionic or ionic surfactants such as for instance sodium lauryl sulfate.

Binders may be selected from, for example, a variety of cellulose derivatives such as hydroxypropyl methylcellulose, hydroxypropyl cellulose, hydroxyethyl cellulose and carboxymethyl-cellulose sodium, polyvinyl pyrrolidone, povidone, sugars, starches, gums, carrageenan and other pharmaceutically acceptable substances with cohesive properties.

Coloring agents may be added for elegance and aesthetics or to differentiate products and may be chosen, for example, from metal oxide pigments or Aluminum Lake dyes.

Glidants may be, for example, colloidal silicon dioxide, talc or the like.

Lubricants may be, for example, talc, magnesium stearate, calcium stearate, stearic acid, sodium stearyl fumarate, sodium benzoate or the like.

Sugars include, for example, simple sugars such as lactose, maltose, mannitol, fructose, sorbitol, sacarose, xylitol, isomaltose, and glucose, as well as complex sugars (polysaccharides) such as maltodextrin, amylodextrin, starches including maize, and modified starches.

Diluents may be, for example, any pharmaceutically acceptable, non-toxic diluent. Particular examples include lactose, dextrose, sucrose, maltose, microcrystalline cellulose, starch, calcium hydrogen phosphate, mannitol and the like. Examples of suitable anti-tacking agents are talc, glycerol monostearate, calcium stearate, colloidal silicon dioxide, glycerin, magnesium stearate, and aluminum stearate.

Optionally about 0 to about 90% by weight pharmaceutical compression aid, and/or about 0 to about 80% by weight of a pharmaceutical extrusion aid such as microcrystalline cellulose and/or pectin may be used.

The pharmaceutical compression aid may be selected from the group consisting of microcrystalline cellulose, lactose, cellulose, dibasic calcium phosphate dihydrate, calcium sulfite dihydrate, tricalcium phosphate and compressible sugar. The capsule, tablet, pellet or bead of pregabalin may optionally comprise excipients, lubricants, binders or glidants. Some examples of disintegrating agents are Crospovidone™ (ie. homopolymer cross-linked N-vinyl-2-pyrrolidone), sodium starch glycolate, Croscarmelose™ (ie. cross-linked sodium carboxymethylcellulose), and the like and mixtures thereof.

Examples of plasticizers that may be used in the formulation include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The typical plasticizers are triacetin, acetylated monoglyceride, acetyltributylcitrate, acetyltriethylcitrate, glycerin sorbitol, diethyloxalate, diethylmalate, diethylphthalate, diethylfumarate, dibutylsuccinate, diethylmalonate, dioctylphthalate, dibutylsebacate, triethylcitrate, tributylcitrate, glyceroltributyrate, polyethylene glycol, glycerol, vegetable and mineral oils and the like. Depending on the particular plasticizer, amounts of from 0 to about 25%, and typically about 0.1% to about 20% of the plasticizer can be used.

Examples of other additives that may be used as part of the formulations described herein include, but are not limited to disintegrants, carbohydrates, sugars, sucrose, sorbitol, mannitol, zinc salts, tannic acid salts; salts of acids and bases such as sodium and potassium phosphates, sodium and potassium hydroxide, sodium and potassium carbonates and bicarbonates; acids such as hydrochloric acid, sulfuric acid, nitric acid, lactic acid, phosphoric acid, citric acid, malic acid, fumaric acid, stearic acid, tartaric acid, boric acid, borax, and benzoic acid.

Examples of disintegrants include: alginic acid, carboxymethylcellulose calcium, carboxymethylcellulose sodium, colloidal silicon dioxide, croscarmellose sodium, crospovidone, primogel, guar gum, magnesium aluminum silicate, methylcellulose, microcrystalline cellulose, polyacrilin potassium, powdered cellulose, pregelatinized starch, sodium alginate and starch.

The wicking agents may be selected from the group comprising hydrophilic, organic, polymeric, fusible substance or a particulate soluble or insoluble inorganic material. Suitable hydrophilic, organic, fusible wicking agents include, for example, polyethylene glycols (PEGs) of various molecular weights e.g. 1,000 to 20,000 typically 4,000 to 10,000 and suitable particulate inorganic wicking agents include, for example, dicalcium phosphate and lactose. Other examples of wicking agents include high HLB surfactants (for example Tween 20, Tween 60 or Tween 80; ethylene oxide propylene oxide block copolymers, ionic surfactants such as sodium lauryl sulfate, sodium docusate, non-swelling hydrophilic polymers such as cellulose ethers, complexing agents such as: polyvinyl pyrrolidone, cyclodextrins and non-ionic surface active agents; and micelle forming agents, which may be surface active agents such as Tweens (Poly (ethylene Oxide) modified sorbitan monoesters), Spans (fatty acid sorbitan esters), sodium lauryl sulfate and sodium docusate.

The compositions may be formulated to be compatible and result in stable products.

Figure 7:
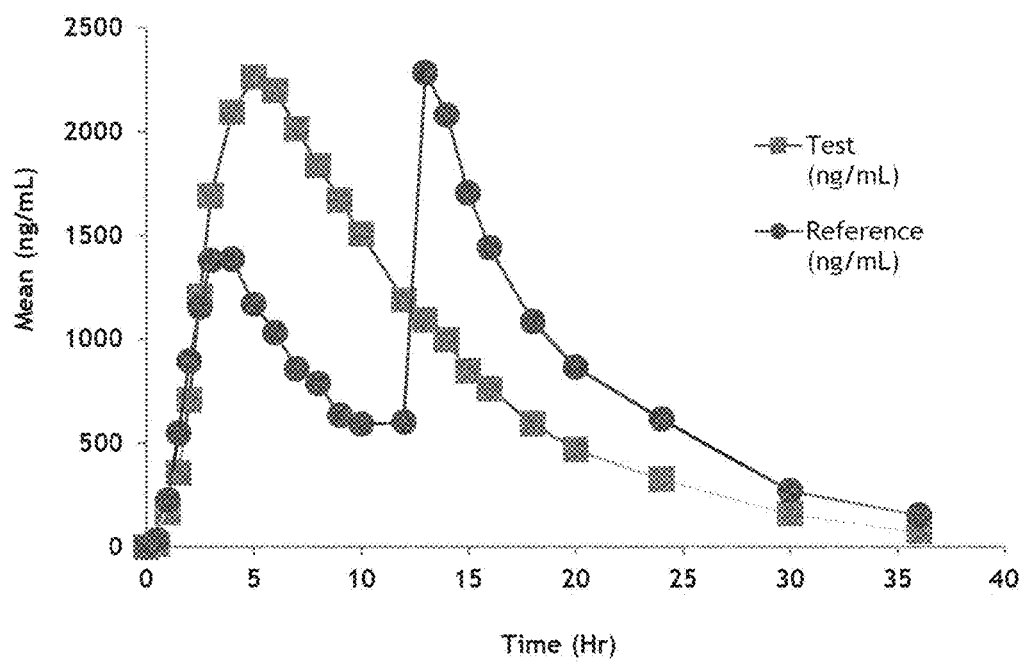
FIG. 7 shows a comparative oral bioavailability study of 165 mg once-a-day pregabalin controlled extended release capsules (Test) versus 75 mg LYRICA™ (pregabalin) immediate release capsules (Reference) administered two times a day in normal healthy, adult, human subjects under fed conditions, wherein the pregabalin controlled extended release capsules have a higher exposure in the first 12 hours after dosing.

In an embodiment (see Example 1 and FIG. 7), wherein, on once daily dosing with meals, the following plasma concentrations ±30% are obtained, and time to maximum concentration of 5.0±40%, half life is 6.0±40% and rate at which said at least one API is removed in the body is 0.1±40%:

| Time (Hours) | Mean Plasma Test (ng/mL) | Coefficient of Variation Test (ng/mL) |
| --- | --- | --- |
| 0 | 0 | Missing |
| 0.5 | 13 | 32 |
| 1.0 | 165 | 108 |
| 1.5 | 356 | 93 |
| 2.0 | 706 | 83 |
| 2.5 | 1209 | 46 |
| 3.0 | 1692 | 42 |
| 4.0 | 2093 | 20 |
| 5.0 | 2262 | 14 |
| 6.0 | 2197 | 13 |
| 7.0 | 2013 | 13 |
| 8.0 | 1837 | 16 |
| 9.0 | 1670 | 16 |
| 10.0 | 1509 | 25 |
| 12.0 | 1189 | 30 |
| 13.0 | 1092 | 24 |
| 14.0 | 998 | 25 |
| 15.0 | 846 | 28 |
| 16.0 | 760 | 26 |
| 18.0 | 593 | 26 |
| 20.0 | 468 | 29 |
| 24.0 | 326 | 37 |
| 30.0 | 162 | 28 |
| 36.0 | 75 | 28 |

Figure 8:
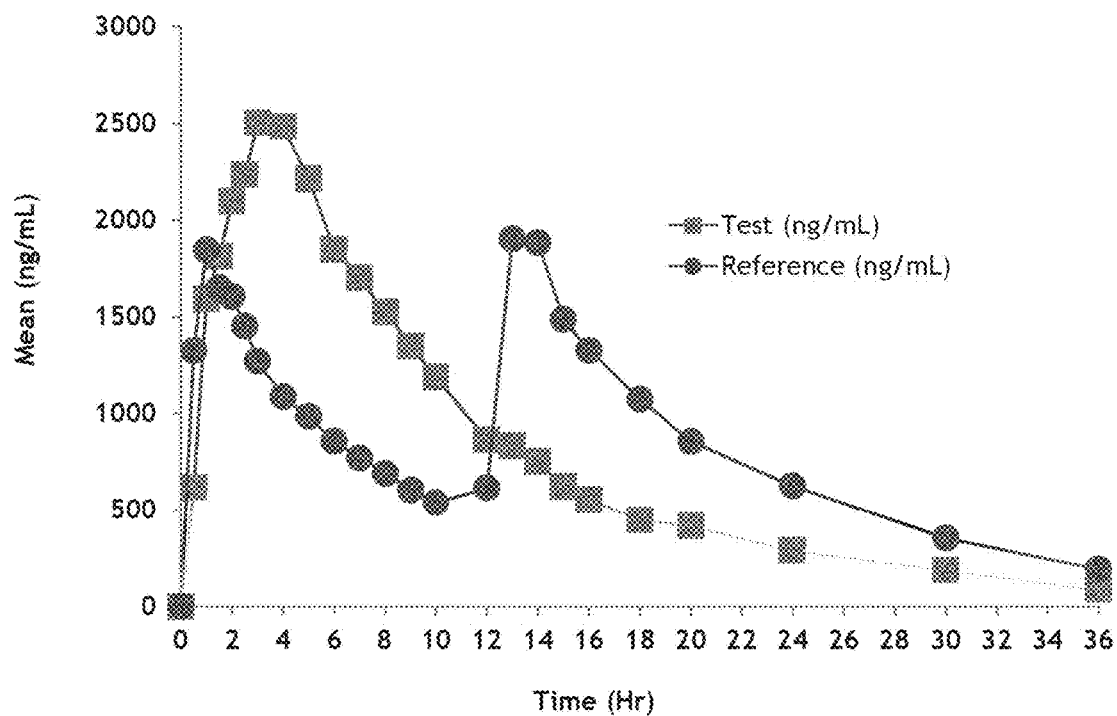
FIG. 8 shows a comparative oral bioavailability study of 165 mg once-a-day pregabalin controlled extended release capsules (Test) versus 75 mg LYRICA™ (pregabalin) immediate release capsules (Reference) administered two times a day in normal healthy, adult, human subjects under fasting conditions, wherein the pregabalin controlled extended release capsules have a higher exposure in the first 12 hours after dosing.

In another embodiment (see Example 1 and FIG. 8), wherein, on once daily dosing without meals, the following plasma concentrations ±40%, and time to maximum concentration of 3.0±40%, half life is 7.2±40% and rate at which said at least one API is removed in the body is 0.1±40%:

| Time (Hours) | Mean Plasma Test (ng/mL) | Coefficient of Variation Test (ng/mL) |
| --- | --- | --- |
| 0.0 | 0 | Missing |
| 0.5 | 616 | 96 |
| 1.0 | 1590 | 48 |
| 1.5 | 1811 | 43 |
| 2.0 | 2100 | 32 |
| 2.5 | 2237 | 24 |
| 3.0 | 2504 | 21 |
| 4.0 | 2484 | 14 |
| 5.0 | 2216 | 23 |
| 6.0 | 1845 | 20 |
| 7.0 | 1700 | 26 |
| 8.0 | 1523 | 25 |
| 9.0 | 1348 | 28 |
| 10.0 | 1188 | 30 |
| 12.0 | 863 | 23 |
| 13.0 | 834 | 40 |
| 14.0 | 751 | 39 |
| 15.0 | 621 | 40 |
| 16.0 | 554 | 46 |
| 18.0 | 449 | 46 |
| 20.00 | 417 | 50 |
| 24.00 | 291 | 56 |
| 30.00 | 190 | 75 |
| 36.00 | 90 | 58 |

Figure 9:
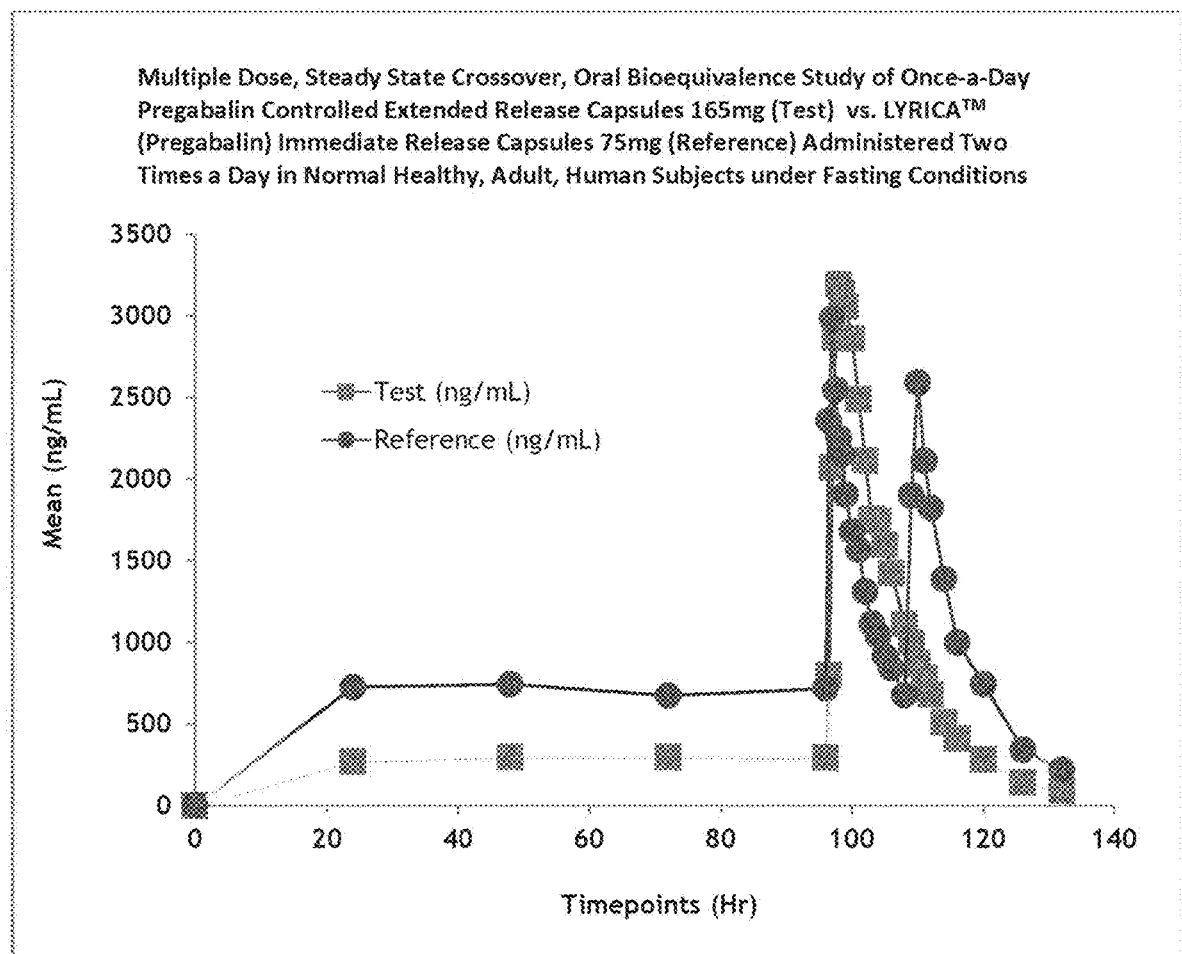
FIG. 9 shows the result of an open label, balanced, randomized, two treatment, two sequence, two period, multiple dose, steady state crossover, oral bioequivalence study of 165 mg once-a-day pregabalin controlled extended release capsules (Test) versus 75 mg LYRICA™ (pregabalin) immediate release capsules (Reference) administered two times a day in normal healthy, adult, human subjects under fasting conditions, wherein the pregabalin controlled extended release capsules have a higher exposure in the first 12 hours after dosing.

In another embodiment (see Example 1 and FIG. 9), wherein, on once daily multiple dosing steady state without meals, the following plasma concentrations ±30%, and time to maximum concentration of 98.5±40%, minimum concentration is 91.0±40% and average concentration is 1088±40%:

| Time (Hours) | Mean Plasma Test (ng/mL) | Coefficient of Variation Test (ng/mL) |
| --- | --- | --- |
| 0.0 | 0.0 | Missing |
| 24.0 | 272 | 31 |
| 48.0 | 296 | 32 |
| 72.0 | 296 | 29 |
| 96.0 | 293 | 31 |
| 96.5 | 798 | 80 |
| 97.0 | 2070 | 51 |
| 97.5 | 2863 | 32 |
| 98.0 | 3189 | 24 |
| 98.5 | 3136 | 15 |
| 99.0 | 3053 | 14 |
| 100.0 | 2860 | 14 |
| 101.0 | 2489 | 18 |
| 102.0 | 2115 | 20 |
| 103.0 | 1755 | 24 |
| 104.0 | 1743 | 19 |
| 105.0 | 1594 | 17 |
| 106.0 | 1421 | 20 |
| 108.0 | 1110 | 22 |
| 109.0 | 995 | 22 |
| 110.0 | 870 | 25 |
| 111.0 | 780 | 23 |
| 112.0 | 682 | 25 |
| 114.0 | 508 | 26 |
| 116.0 | 410 | 30 |
| 120.0 | 282 | 30 |
| 126.0 | 143 | 37 |
| 132.0 | 91 | 52 |

Figure 11:
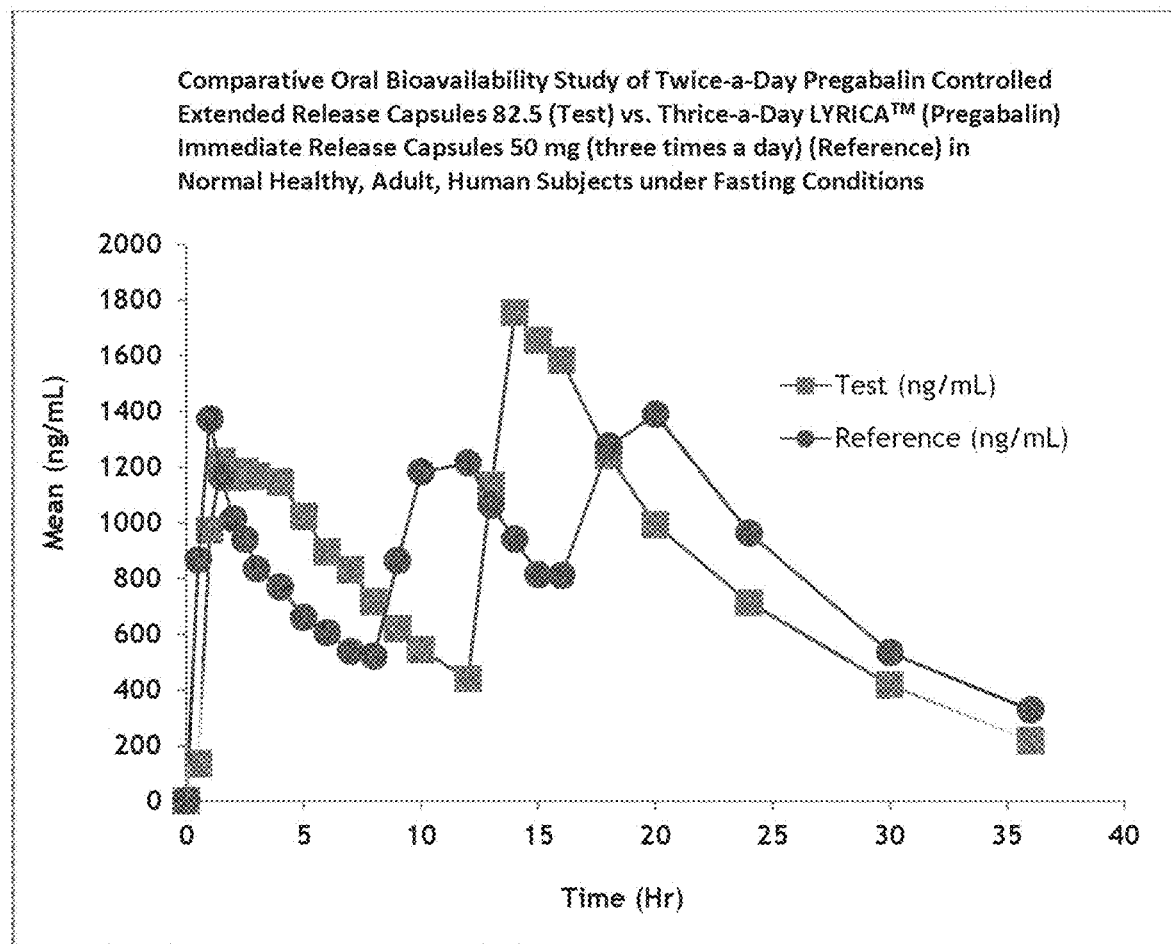
FIG. 11 shows the result of an open label, randomized, two treatment, two sequence, two period, cross over, comparative oral bioavailability study of 82.5 mg twice-a-day pregabalin controlled extended release capsules (Test) versus 50 mg thrice-a-day LYRICA™ (pregabalin) immediate release capsules (Reference) in normal healthy, adult, human subjects under fasting conditions, wherein the pregabalin controlled extended release capsules have similar bioequivalency, but higher exposure, to LYRICA™ (pregabalin) immediate release capsules.

In another embodiment (see Example 1 and FIG. 11), wherein, on twice daily dosing without meals, the following plasma concentrations ±40% are obtained, and time to maximum concentration of 14.0±40%, half life is 7.1±40% and rate at which said at least one API is removed in the body is 0.1±40%:

| Time (Hours) | Mean Plasma Test (ng/mL) | Coefficient of Variation Test (ng/mL) |
| --- | --- | --- |
| 0.0 | 0.0 | Missing |
| 0.5 | 134 | 106 |
| 1.0 | 972 | 41 |
| 1.5 | 1220 | 34 |
| 2.0 | 1161 | 19 |
| 2.5 | 1182 | 18 |
| 3.0 | 1166 | 25 |
| 4.0 | 1145 | 26 |
| 5.0 | 1023 | 21 |
| 6.0 | 896 | 27 |

| Time (Hours) | Mean Plasma Test (ng/mL) | Coefficient of Variation Test (ng/mL) |
|---|---|---|
| 7.0 | 830 | 31 |
| 8.0 | 716 | 27 |
| 9.0 | 620 | 30 |
| 10.0 | 543 | 30 |
| 12.0 | 440 | 28 |
| 13.0 | 1134 | 49 |
| 14.0 | 1754 | 17 |
| 15.0 | 1653 | 20 |
| 16.0 | 1582 | 29 |
| 18.0 | 1240 | 24 |
| 20.0 | 991.5 | 30 |
| 24.0 | 713 | 29 |
| 30.0 | 417 | 35 |
| 36.0 | 217 | 35 |

Figure 12:
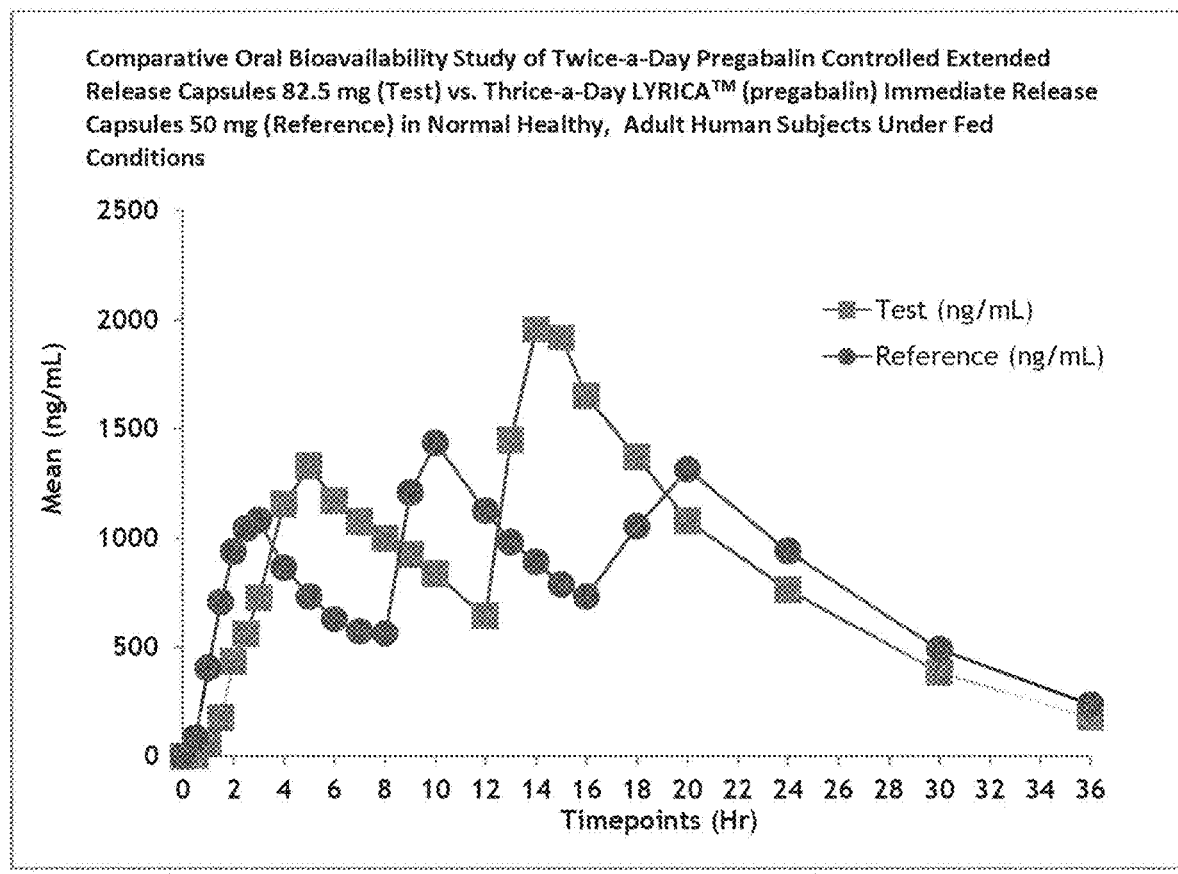
FIG. 12 shows the result of a comparative oral bioavailability study of 82.5 mg twice-a-day pregabalin controlled extended release capsules (Test) versus 50 mg thrice-a-day LYRICA™ (pregabalin) immediate release capsules (Reference) in normal healthy, adult, human subjects under fed conditions, wherein the pregabalin controlled extended release capsules have similar bioequivalency, but higher exposure, to LYRICA™ (pregabalin) immediate release capsules.

In another embodiment (see Example 1 and FIG. 12), wherein, on twice daily dosing with meals, the following plasma concentrations ±40% are obtained, and time to maximum concentration of 14.0±40%, half life is 5.9±40% and rate at which said at least one API is removed in the body is 0.1±40%:

| Time (Hours) | Mean Plasma Test (ng/mL) | Coefficient of Variation Test (ng/mL) |
|---|---|---|
| 0.0 | 0 | Missing |
| 0.5 | 4 | 346 |
| 1.0 | 56 | 219 |
| 1.5 | 177 | 114 |
| 2.0 | 433 | 64 |
| 2.5 | 561 | 56 |
| 3.0 | 728 | 49 |
| 4.0 | 1155 | 43 |
| 5.0 | 1332 | 23 |
| 6.0 | 1170 | 18 |
| 7.0 | 1075 | 18 |
| 8.0 | 999 | 19 |
| 9.0 | 924 | 27 |
| 10.0 | 837 | 26 |
| 12.0 | 642 | 29 |
| 13.0 | 1450 | 31 |
| 14.0 | 1956 | 20 |
| 15.0 | 1918 | 22 |
| 16.0 | 1649 | 25 |
| 18.0 | 1370 | 23 |
| 20.0 | 1078 | 21 |
| 24.0 | 765 | 26 |
| 30.0 | 383 | 24 |
| 36.0 | 178 | 31 |

Figure 10:
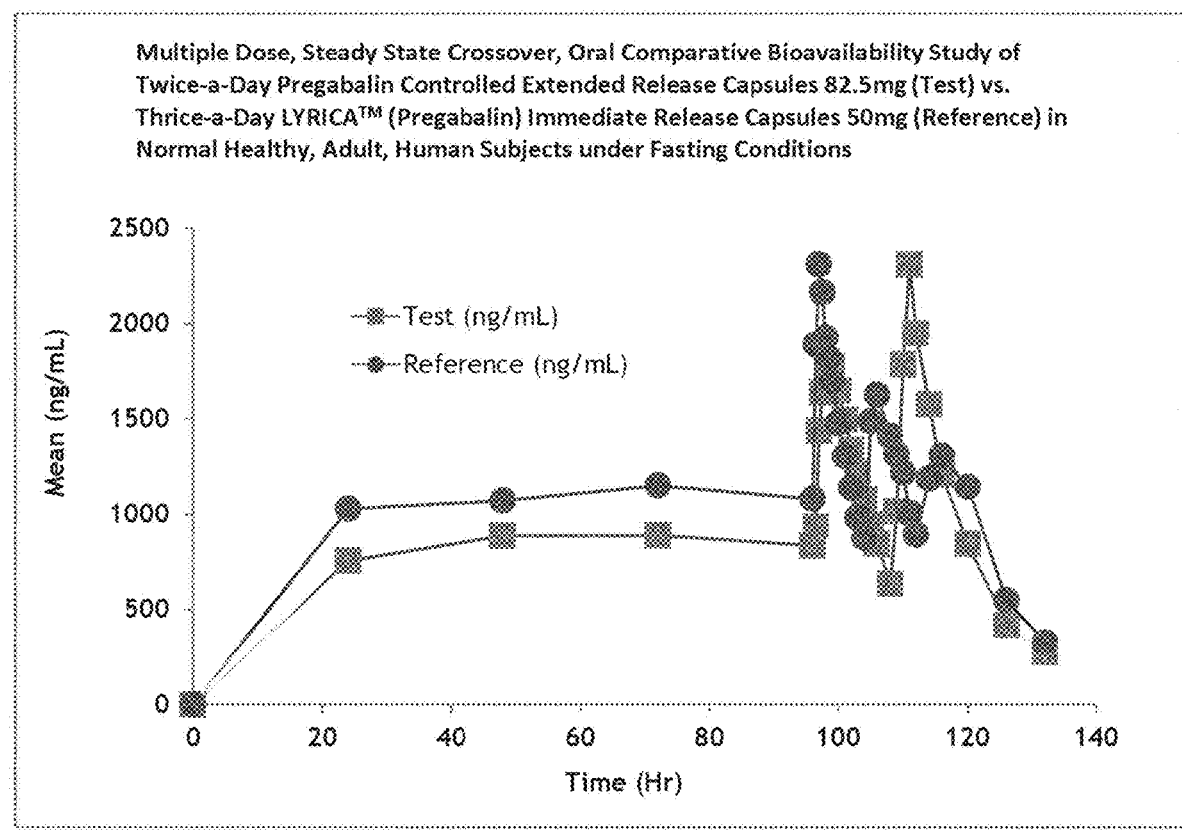
FIG. 10 shows the result of an open label, balanced, randomized, two treatment, two sequence, two period, multiple dose, steady state crossover, oral comparative bioavailability study of 82.5 mg twice-a-day pregabalin controlled extended release capsules (Test) versus 50 mg thrice-a-day LYRICA™ (pregabalin) immediate release capsules (Reference) in normal healthy, adult, human subjects under fasting conditions, wherein the pregabalin controlled extended release capsules have similar bioequivalency to LYRICA™ (pregabalin) immediate release capsules.

In another embodiment (see Example 1 and FIG. 10), wherein, on once daily multiple dosing steady state without meals, the following plasma concentrations ±40%, and time to maximum concentration of 111.0±40%, minimum concentration is 274.5±40% and average concentration is 1041±40%:

| Time (Hours) | Mean Plasma Test (ng/mL) | Coefficient of Variation Test (ng/mL) |
|---|---|---|
| 0.0 | 0.0 | Missing |
| 24.0 | 756 | 18 |
| 48.0 | 887 | 26 |
| 72.0 | 889 | 22 |
| 96.0 | 836 | 22 |
| 96.5 | 936 | 16 |
| 97.0 | 1436 | 29 |
| 97.5 | 1636 | 25 |
| 98.0 | 1639 | 20 |
| 98.5 | 1703 | 18 |
| 99.0 | 1776 | 17 |
| 100.0 | 1647 | 21 |
| 101.0 | 1495 | 22 |
| 102.0 | 1338 | 22 |
| 103.0 | 1207 | 27 |
| 104.0 | 1077 | 24 |
| 105.0 | 945 | 26 |
| 106.0 | 842 | 24 |
| 108.0 | 636 | 25 |
| 109.0 | 1016 | 40 |
| 110.0 | 1784 | 27 |
| 111.0 | 2311 | 16 |
| 112.0 | 1948 | 15 |
| 114.0 | 1576 | 21 |
| 116.0 | 1206 | 19 |
| 120.0 | 844 | 18 |
| 126.0 | 417 | 24 |
| 132.0 | 274 | 28 |

In another embodiment, wherein the composition has the following dissolution time-percent release profile:

| Time [Min] | % Pregabalin released |
|---|---|
| 0 | 0 |
| 60 | 41 ± 30% |
| 70 | 73 ± 30% |
| 80 | 75 ± 25% |
| 90 | 77 ± 25% |
| 120 | 80 ± 25% |
| 150 | 83 ± 10% |
| 180 | 85 ± 10% |
| 240 | 89 ± 10% |
| 300 | 92 ± 10% |
| 360 | 94 ± 10% |

In another embodiment, wherein the pH-dependent populations of unit dosage forms of pregabalin coated beads, pellets, tablets and/or granules has the following dissolution time-percent release profile:

| Time [Hr] | % Pregabalin released |
|---|---|
| 0 | 0 |
| 1 | 20 ± 30% |
| 2 | 43 ± 30% |
| 3 | 102 ± 10% |
| 4 | 105 ± 10% |
| 5 | 106.0 ± 10% |
| 6 | 106 ± 10% |
| 7 | 106 ± 10% |
| 8 | 107 ± 10% |

In another embodiment, wherein the pH-independent populations of unit dosage forms of pregabalin coated beads, pellets, tablets and/or granules has the following dissolution time-percent release profile:

| Time [Hr] | % Pregabalin released |
|---|---|
| 0 | 0 |
| 1 | 63 ± 30% |
| 2 | 82 ± 30% |
| 3 | 91 ± 10% |
| 4 | 97 ± 10% |
| 5 | 101 ± 10% |
| 6 | 102 ± 10% |
| 7 | 103 ± 10% |
| 8 | 104 ± 10% |
| 9 | 105 ± 10% |
| 10 | 105 ± 10% |
| 11 | 105 ± 10% |
| 12 | 107 ± 10% |

Figure 13:
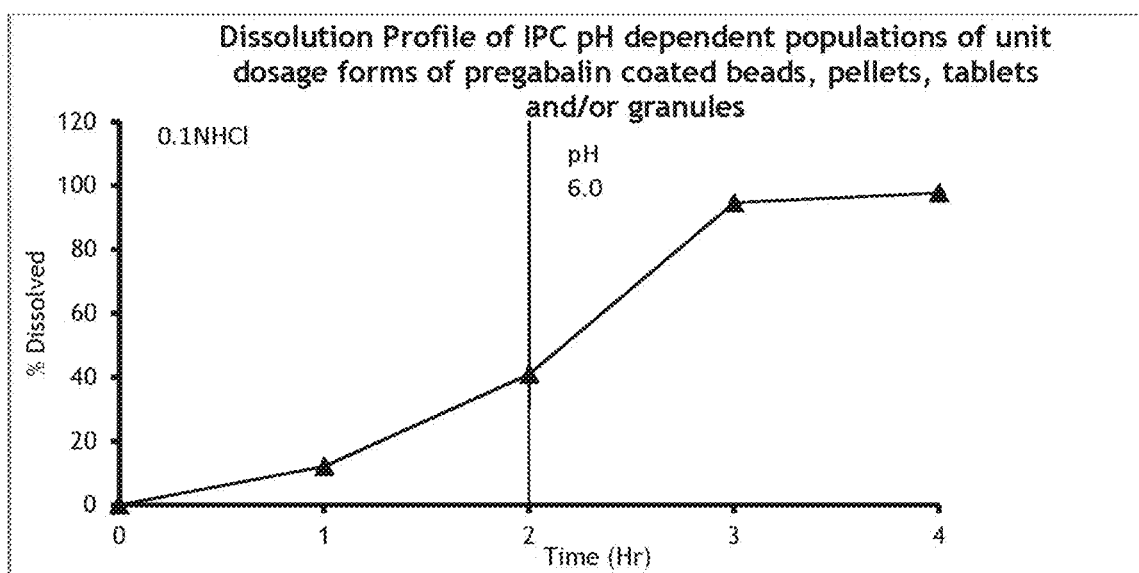
FIG. 13 shows an example of a dissolution profile of IPC pH-dependent populations of unit dosage forms of pregabalin coated beads, pellets, tablets and/or granules.

In another embodiment (see Example 11 and FIG. 13), wherein the pH-dependent populations of unit dosage forms of pregabalin coated beads, pellets, tablets and/or granules has the following dissolution time-percent release profile:

| Time [Hr] | % Pregabalin released |
|---|---|
| 0 | 0 |
| 1 | 12 ± 30% |
| 2 | 41 ± 30% |
| 3 | 95 ± 15% |
| 4 | 98 ± 10% |

Figure 14:
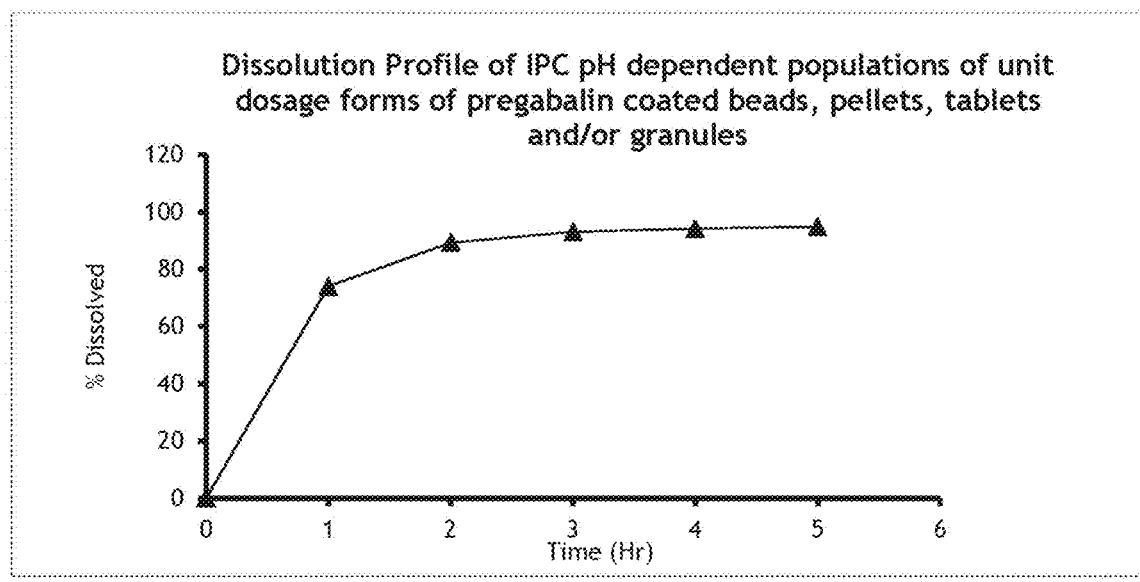
FIG. 14 shows another example of a dissolution profile of IPC pH-dependent populations of unit dosage forms of pregabalin coated beads, pellets, tablets and/or granules.

In another embodiment (see Example 11 and FIG. 14), wherein the pH-independent populations of unit dosage forms of pregabalin coated beads, pellets, tablets and/or granules has the following dissolution time-percent released profile:

| Time [Hr] | % Pregabalin released |
|---|---|
| 0 | 0 |
| 1 | 74 ± 20% |
| 2 | 89 ± 15% |
| 3 | 93 ± 15% |
| 4 | 94 ± 15% |
| 5 | 95 ± 15% |

In another embodiment (see Example 11), wherein the unit dosage forms of the pregabalin control release capsule has the following dissolution time-percent release profile:

| Time [Hr] | % Pregabalin released |
|---|---|
| 0 | 0 |
| 1 | 52 ± 30% |
| 2 | 80 ± 30% |
| 3 | 97 ± 25% |
| 4 | 97 ± 20% |
| 5 | 97 ± 10% |
| 6 | 98 ± 10% |

Method of Treatment/Uses of the Controlled Extended Release Compositions

The compositions/formulations described herein may be used to treat a condition or disorder in a subject that is responsive to pregabalin. For example, the compositions described herein may be used for the management of neuropathic pain associated with diabetic peripheral neuropathy, management of post herpetic neuralgia, management of fibromyalgia, and as an adjunctive therapy for adult patients with partial onset seizures. It may also be useful as antiseizure therapy for central nervous system disorders such as epilepsy, Hunitngton's chorea, cerebral ischemia, Parkinson's disease, tardive dyskinesia, and spasticity. It may exhibit anti-seizure activity and be useful for treating, among other conditions, epilepsy, pain, physiological conditions associated with psychomotor stimulants, inflammation, GI damage, alcoholism, insomnia, fibromyalgia, and various psychiatric disorders, including anxiety, depression, mania, and bipolar disorder.

Oral administration of the composition to the subject may be once- or twice-a-day with or without a meal. The composition may, therefore, be a chronotherapeutic controlled extended release composition. The composition may, therefore, be designed to take into consideration the symptomatology and chronobiology of a condition or disorder in a subject that is responsive to pregabalin (e.g. fibromyalgia) thus allowing for dosing at any time (e.g. when symptoms are high). Therefore, the composition may be taken following, during or after a meal. The composition may improve patient compliance and efficacy in the treatment of pain, sleep, fatigue and other comorbidities, including depression, and reduce side effect profiles encountered by fibromyalgia patients.

In an embodiment, a condition or disorder in a subject that is responsive to pregabalin is treated using a pregabalin controlled extended release formulation described herein with at least one of the following dosage strengths: about 37.5 mg, about 41.25 mg, about 75 mg, about 82.5 mg, about 150 mg, about 165 mg, about 300 mg, about 330 mg, about 450 mg, about 495 mg, about 600 mg, and/or about 660 mg, wherein each dosage strength contains one distinct population of delayed timed release pregabalin contributing between about 10% to about 90% of pregabalin (and/or other forms of pregablin described herein), and another distinct population of controlled timed release pregabalin contributing between about 90% to about 10% of pregabalin (and/or other forms of pregablin described herein). In another embodiment, each dosage strength contains one distinct population of delayed timed release pregabalin contributing between about 30% to about 40% of pregabalin (and/or other forms of pregabalin described herein), and another distinct population of controlled timed release pregabalin contributing between about 70% to about 60% of pregabalin (and/or other forms of pregablin described herein).

In certain embodiments, the pregabalin may be released and absorbed within the place in the upper small intestine where most of L-amino acid transporters reside, but not beyond the hepatic flexure. The compositions described herein, when ingested in the presence or absence of food, can be capable of releasing its pregabalin content in a timed controlled extended release stepwise manner for a more precise control of the release of pregabalin within the place in the upper small intestine, but, typically, not beyond the hepatic flexure, thus extending the period of time during which pregabalin is released in the GI tract, effectively widening the absorption window associated with immediate release dosing, thereby permitting once-a-day dosing. This also results in higher exposure in about the first 12 hours than would be expected with immediate release pregabalin dosed twice-a-day. In another embodiment, there may be significantly higher pregabalin exposure when administered once-a-day or twice-a-day. In a further embodiment, following once-a-day administration of pregabalin, there may be significantly higher exposure to pregabalin, at least within about the first twelve hours of administration, compared to commercial immediate release preparations taken two times-a-day. In another embodiment, the once-a-day oral administration of pregabalin with the meal (e.g. evening meal) has a similar bioequivalency to immediate release formulation of pregabalin e.g., LYRICA™ administered twice-a-day. In a further embodiment, the composition does not promote undesirable lactam formation.

The compositions comprising the unit dosage form(s), including population(s) of unit dosage forms, described herein may be placed in a housing suitable for oral application such as, for example, a capsule (e.g., hard gelatin capsule). The capsule dosage form may be administered one to two times a day depending on the formulation provided within the capsule. The typical daily dose of pregabalin may vary and will depend on various factors such as the individual requirements of the patients, the mode of administration and the disease. In general the daily dose will be in the range of about 10 to about 1200 mg of pregabalin. For example, the daily dose may be about 37.5 mg, about 41.25 mg, about 75 mg, about 82.5 mg, about 150 mg, about 165 mg, about 300 mg, about 330 mg, about 450 mg, about 495 mg, about 600 mg and about 660 mg. The preparation according to aspects described herein is also suitable for dispersion in an aqueous liquid with neutral or slightly acidic pH-value before being orally administered or fed through a naso-gastric tube.

When administered as a solid formulation, such as a capsule, the composition described herein, unlike commercial immediate release formulation and flotation/gastroretentive compositions, may release its pregabalin content in timed controlled extended release stepwise manner for a more precise control of the release of pregabalin within the place in the upper small intestine where most of L-amino acid transporters reside, but, typically, not beyond the hepatic flexure, thus extending the period of time during which pregabalin is released in the GI tract, effectively widening the absorption window associated with immediate release dosing or floatation/gastroretentive devices, thereby permitting once-a-day dosing.

Typically, the composition is administered in an amount effective to treat a condition as described herein. The compositions described herein are administered by any suitable route in the form of a pharmaceutical composition adapted to such a route, and in a dose effective for the treatment intended. Therapeutically effective doses of the compositions required to treat the progress of the medical condition are readily ascertained by one of ordinary skill in the art using preclinical and clinical approaches familiar to the medicinal arts.

The composition may be administered orally. Oral administration may involve swallowing, so that the composition enters the GI tract. As mentioned, the composition may also be administered nasogastrically.

The applications, patents and publications described herein are hereby incorporated by reference in their entirety.

When introducing elements disclosed herein, the articles "a", "an", "the", and "said" are intended to mean that there may be one or more of the elements.

Any range described herein is understood to include any incremental ranges or individual values therebetween.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

The expression "at least one of . . . and . . . " is understood to mean one or more of the elements listed; singly or in any combination.

It will be understood that any component defined herein as being included may be explicitly excluded from the claimed invention by way of proviso or negative limitation. For example, in aspects, the composition described herein does not promote undesirable lactam formation Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Pregabalin Controlled Extended Release Capsules

Step 1. Manufacturing of Preqabalin Immediate Release Beads

The Pregabalin Immediate Release (IR) beads with formula shown below was manufactured using powder solution layering technique in a centrifugal coater to give a drug load with a potency of about 70%.

| Ingredients | g | Kg |
| --- | --- | --- |
| Non Pareil sugar beads | 9.25 | 4.625 |
| Pregabalin | 70.00 | 35 |
| Povidone (PVP K30) | 20.00 | 10 |
| Talc | 0.250 | 0.125 |
| Sodium lauryl sulphate | 0.50 | 0.25 |
| Isopropanol | QS | QS |
| Total | 100.00 | 50 |

Step 2. Manufacturing of (pH-dependent Population) Preqabalin Delayed Release (DR) Beads The Pregabalin Immediate Release (IR) beads with a potency of about 70% were coated with a pH-dependent coat in a Uni-Glatt fluid bed coater using a Wurster spray technique, to obtain (pH-dependent population) Pregabalin Delayed Release beads.

Preparation of pH-dependent Coating Suspension

| Ingredients | g |
| --- | --- |
| Pregabalin immediate release beads (potency 70%) | 750 |
| Eudragit L | 37.50 |
| Triethyl citrate | 4.50 |
| Talc | 19.75 |
| Simethicone | 1.15 |
| Water* | QS |

*Water is evaporated during coating

An aqueous dispersion of Eudragit L (Methacrylic Acid—Methyl Methacrylate Copolymer [1:1]) was prepared in a stainless steel vessel using a propeller mixer. The dispersion was fluidized in a fluid bed coater and applied using Wurster coating techniques onto the immediate release pregabalin beads.

Step 3. Manufacturing of (pH-independent Population) Pregabalin Extended Release Beads The Pregabalin Immediate Release (IR) beads with a potency of about 70% were coated with a pH-independent coat in a Uni-Glatt fluid bed coater using a Wurster spray technique, to obtain (pH-independent population) Pregabalin Extended Release beads.

Preparation of Ethylcellulose Extended Release Suspension

| Ingredients | g |
| --- | --- |
| Pregabalin immediate release beads (potency 70%) | 800 |
| Ethylcellulose | 37.50 |
| Hydroxypropylmethyl cellulose | 6.00 |
| Triethyl citrate | 1.50 |
| Talc | 1.50 |
| Ethanol* | QS |

*Ethanol is evaporated during coating

An ethanolic suspension of ethylcellulose was prepared in a stainless steel vessel using a high shear mixer. The suspension was fluidized in a fluid bed coater and applied using Wurster coating techniques onto the immediate release pregabalin beads.

Step 4. Manufacturing of Pregabalin Controlled Extended Release (CXR) Capsules

Pregabalin controlled extended release capsules were made by encapsulating sufficient amounts of pregabalin delayed release beads equivalent to about 30% of the total dose of pregabalin required and sufficient amounts of pregabalin extended release beads equivalent to about 70% of the total dose of pregabalin required into a hard gelatin capsule using a Zanasi 40E encapsulator.

| | Content of pregabalin per capsule | | | | | |
| --- | --- | --- | --- | --- | --- | --- |
| | 41.25 mg Capsule | 82.5 mg Capsule | 165 mg Capsule | 330 mg Capsule | 495 mg Capsule | 660 mg Capsule |
| | Fill weights per capsule ( mg) | | | | | |
| *Amount of Pregabalin delayed release beads | 18.5 | 36.9 | 73.9 | 147.8 | 221.6 | 295.5 |
| Amount of Pregabalin extended release beads | 41.6 | 83.2 | 166.4 | 332.9 | 499.3 | 665.7 |
| Total amount of beads per Capsule | 60.1 | 120.1 | 240.3 | 480.6 | 720.9 | 961.2 |

Figure 2:
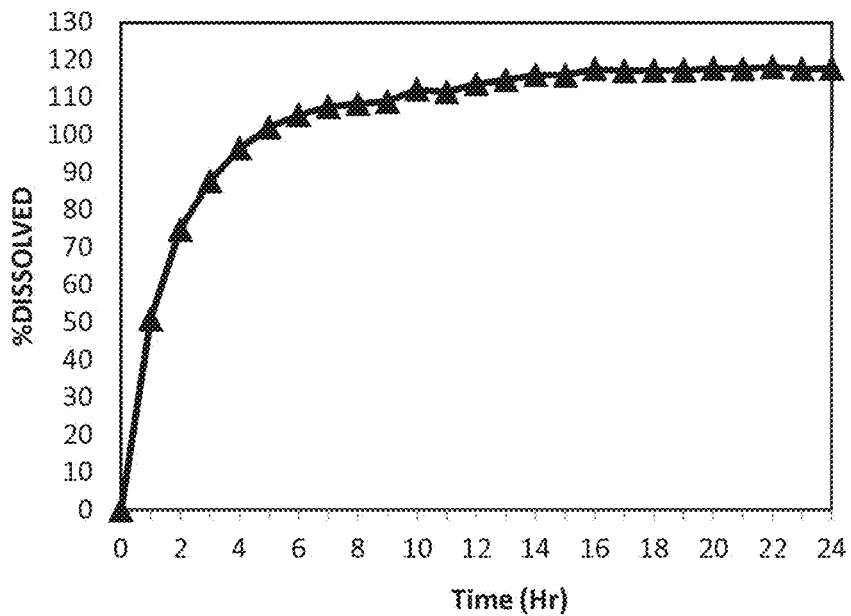
FIG. 2 shows dissolution of 150 mg of pregabalin pH-independent beads from Example 1, at 37° C., 100 rpm in 0.06N HCl for about 24 hours.
Figure 3:
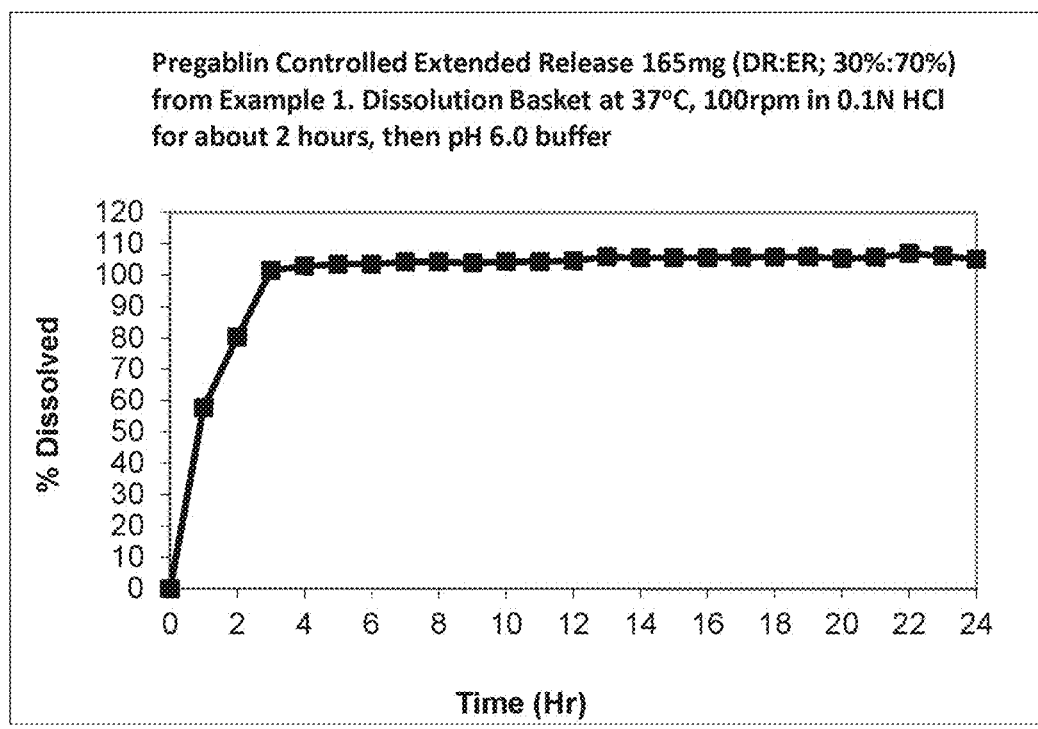
FIG. 3 shows dissolution of 165 mg of pregablin controlled extended release (DR (delayed release):ER (extended release); 30%:70%) from Example 1, at 37° C., 100 rpm in 0.1N HCl for about 2 hours, then pH 6.0 buffer.

Results of dissolution studies are shown in FIGS. 1-3.

TABLE 1

Results from an open label, randomized, two treatment, two sequence, two period, cross over, comparative oral bioavailability study of the 165 mg once-a-day pregabalin controlled extended release capsules of Example 1 and 75 mg LYRICA ® (pregabalin) Immediate Release Capsules (two times a day) from Pfizer Inc. USA, in normal healthy, adult, human subjects under fed conditions. This indicates that the once-a-day pregabalin controlled extended release had similar bioequivalency to twice-a-day LYRICA ® (pregabalin) Immediate Release. (See FIG. 7)

| Description (Pregabalin) | Cmax | AUCt | AUCinf | *Tmax |
| --- | --- | --- | --- | --- |
| LYRICATM (pregabalin) (R) | | | | |
| N | 11 | 11 | 11 | 11 |
| Mean | 2363.0 | 28259.9 | 29629.9 | 13.0 |
| CV (%) | 12.8 | 15.0 | 16.3 | 5.1 |
| Pregabalin (T) | | | | |
| N | 11 | 11 | 11 | 11 |
| Mean | 2449.6 | 28151.8 | 28795.3 | 5.0 |
| CV (%) | 11.8 | 16.3 | 16.3 | 37.3 |
| 90% Confidence Intervals | | | | |
| Lower Limit (%) | 95.6 | 94.8 | 92.4 | |
| Upper Limit (%) | 111.9 | 104.2 | 101.9 | |
| T/R Ratio (%) | 103.5 | 99.4 | 97.0 | |
| Power | 0.9959 | 1.0000 | 0.9999 | |
| Intra Subject Variability | 10.0 | 6.0 | 6.2 | |

*Median of $T_{max}$

TABLE 2

Results from an open label, randomized, two treatment, two sequence, two period, cross over, comparative oral bioavailability study of the 165 mg once-a-day pregabalin controlled extended release capsules of Example 1 and 75 mg LYRICA ™ (pregabalin) Immediate Release Capsules (two times a day) from Pfizer Inc. USA, in normal healthy, adult, human subjects under fasting conditions. This indicates that the once-a-day pregabalin controlled extended release had a higher exposure compared to twice-a-day LYRICA ™ (pregabalin) Immediate Release Capsules. (See FIG. 8)

| Description (Pregabalin) | Cmax | AUCt | AUCinf | *Tmax |
|---|---|---|---|---|
| LYRICA (pregabalin) (R) | | | | |
| N | 12 | 12 | 12 | 12 |
| Mean | 2120.9 | 18096.6 | 20064.1 | 13.5 |
| CV (%) | 17.7 | 22.9 | 25.8 | 10.1 |
| Pregabalin (T) | | | | |
| N | 12 | 12 | 12 | 12 |
| Mean | 2844.0 | 28444.5 | 29420.8 | 3.0 |
| CV (%) | 9.3 | 22.1 | 23.5 | 36.7 |
| 90% Confidence Intervals | | | | |
| Lower Limit (%) | 125.4 | 151.4 | 141.0 | |
| Upper Limit (%) | 146.2 | 163.8 | 153.9 | |
| T/R Ratio (%) | 135.4 | 157.5 | 147.3 | |
| Power | 0.9969 | 1.0000 | 1.0000 | |
| Intra Subject Variability | 10.4 | 5.3 | 5.9 | |

*Median of $T_{max}$

TABLE 3

Results from a multiple dose, steady state crossover, oral bioequivalence study of the 165 mg once-a-day pregabalin controlled extended release capsules of Example 1 and 75 mg LYRICA ™ (pregabalin) Immediate Release Capsules taken two times a day in normal healthy, adult, human subjects under fasting conditions. This indicates that the once-a-day pregabalin controlled extended release had similar bioequivalency to twice-a-day LYRICA ™ (pregabalin) Immediate Release Capsules. (See FIG. 9)

| Description (Pregabalin) | Cmax | AUC(0-τ) | Cmin | *Tmax | Cavg |
|---|---|---|---|---|---|
| LYRICA ® (Pregabalin) (R) | | | | | |
| N | 16 | 16 | 16 | 16 | 16 |
| Mean | 3277.8 | 39171.3 | 209.2 | 97.0 | 1088.1 |
| CV (%) | 17.1 | 16.8 | 40.0 | 5.6 | 16.8 |
| Pregabalin (T) | | | | | |
| N | 16 | 16 | 16 | 16 | 16 |
| Mean | 3519.4 | 33198.9 | 91.0 | 98.5 | 922.2 |
| CV (%) | 17.5 | 17.1 | 52.2 | 0.9 | 17.1 |
| 90% Confidence Intervals | | | | | |
| Lower Limit (%) | 99.5 | 81.0 | | | |
| Upper Limit (%) | 116.0 | 88.5 | | | |
| T/R Ratio (%) | 107.4 | 84.7 | | | |
| Power | 0.9976 | 1.0000 | | | |
| Intra Subject Variability | 12.4 | 7.1 | | | |

*Median of $T_{max}$

TABLE 4

Results from an open label, balanced, randomized, two treatment, two sequence, two period, multiple dose, steady state crossover, oral comparative bioavailability study of the 82.5 mg twice-a-day pregabalin controlled extended release capsules of Example 1 versus 50 mg LYRICA ™ (pregabalin) Immediate Release Capsules (three times a day) in healthy, adult, human, subjects under fasting conditions. This indicates that the twice-a-day pregabalin controlled extended release had similar bioequivalency to thrice-a-day LYRICA ™ (pregabalin) Immediate Release Capsules. (See FIG. 10)

| Description (Pregabalin) | Cmax | AUC(0-τ) | Cmin | *Tmax | Cavg |
|---|---|---|---|---|---|
| LYRICA ® (Pregabalin) (R) | | | | | |
| N | 16 | 16 | 16 | 16 | 16 |
| Mean | 2610.3 | 39558.0 | 315.1 | 97.0 | 1098.8 |
| CV (%) | 18.5 | 13.9 | 34.6 | 2.1 | 13.9 |
| Pregabalin (T) | | | | | |
| N | 16 | 16 | 16 | 16 | 16 |
| Mean | 2371.6 | 37487.8 | 274.5 | 111.0 | 1041.3 |
| CV (%) | 12.1 | 16.5 | 28.4 | 3.2 | 16.5 |
| 90% Confidence Intervals | | | | | |
| Lower Limit (%) | 85.8 | 91.2 | | | |
| Upper Limit (%) | 98.1 | 97.9 | | | |
| T/R Ratio (%) | 91.8 | 94.5 | | | |
| Power | 0.9995 | 1.0000 | | | |
| Intra Subject Variability | 10.7 | 5.7 | | | |

*Median of $T_{max}$

TABLE 5

Shows the result of an open label, randomized, two treatment, two sequence, two period, cross over, comparative oral bioavailability study of the 82.5 mg twice-a-day pregabalin controlled extended release capsules of Example 1 versus 50 mg LYRICA ™ (pregabalin) Immediate Release Capsules (three times a day) in healthy, adult, human, subjects under fasting conditions. This indicates that the twice-a-day pregabalin controlled extended release had similar bioavailability, but higher exposure, to thrice-a-day LYRICA ™ (pregabalin) Immediate Release Capsules. (See FIG. 11)

| Description (Pregabalin) | Cmax | AUCt | AUCinf | *Tmax |
|---|---|---|---|---|
| LYRICA (pregabalin) (R) | | | | |
| N | 11 | 11 | 11 | 11 |
| Mean | 1549.7 | 16381.2 | 19641.9 | 20.0 |
| CV (%) | 20.8 | 26.0 | 29.3 | 10.4 |
| Pregabalin (T) | | | | |
| N | 11 | 11 | 11 | 11 |
| Mean | 1929.9 | 19306.2 | 21568.2 | 14.0 |
| CV (%) | 17.3 | 23.3 | 25.1 | 7.8 |
| 90% Confidence Intervals | | | | |
| Lower Limit (%) | 114.4 | 106.8 | 99.8 | |
| Upper Limit (%) | 137.2 | 131.2 | 122.2 | |
| T/R Ratio (%) | 125.3 | 118.3 | 110.4 | |
| Power | 0.9874 | 0.9694 | 0.9730 | |
| Intra Subject Variability | 11.6 | 13.2 | 12.9 | |

*Median of $T_{max}$

TABLE 6

Shows the result of an open label, randomized, two treatment, two sequence, two period, cross over, comparative oral bioavailability study of the 82.5 mg twice-a-day pregabalin controlled extended release capsules of Example 1 versus 50 mg LYRICA™ (pregabalin) Immediate Release Capsules (three times a day) in healthy, adult, human, subjects under fed conditions. This indicates that the twice-a-day pregabalin controlled extended release had similar bioavailability to thrice-a-day LYRICA™ (pregabalin) Immediate Release Capsules. (see FIG. 12)

| Description (Pregabalin) | Cmax | AUCt | AUCinf | *Tmax |
|---|---|---|---|---|
| LYRICA ® (pregabalin) (R) | | | | |
| N | 12 | 12 | 12 | 12 |
| Mean | 1574.9 | 28978.5 | 31091.4 | 10.0 |
| CV (%) | 11.1 | 13.5 | 14.1 | 46.4 |
| Pregabalin (T) | | | | |
| N | 12 | 12 | 12 | 12 |
| Mean | 2095.8 | 30525.3 | 32061.8 | 14.0 |
| CV (%) | 20.8 | 16.4 | 16.9 | 30.4 |
| 90% Confidence Intervals | | | | |
| Lower Limit (%) | 116.3 | 101.1 | 99.2 | |
| Upper Limit (%) | 148.3 | 109.0 | 106.5 | |
| T/R Ratio (%) | 1.3 | 1.0 | 1.0 | |
| Power | 0.9193 | 1.0000 | 1.0000 | |
| Intra Subject Variability | 0.2 | 0.1 | 0.1 | |

*Median of $T_{max}$

TABLE 6A

Shows, for Example 1, the result of, once daily dosing with meals, the following plasma concentrations ± 30% were obtained, and time to maximum concentration of about 5.0 ± 40%, half life was 6.0 ± 40% and rate at which said at least one API was removed in the body was 0.1 ± 40% (see FIG. 7):

| Time (Hours) | Mean Plasma Test (ng/mL) | Coefficient of Variation Test (ng/mL) |
|---|---|---|
| 0 | 0 | Missing |
| 0.5 | 13 | 332 |
| 1.0 | 165 | 108 |
| 1.5 | 356 | 93 |
| 2.0 | 706 | 83 |
| 2.5 | 1209 | 46 |
| 3.0 | 1692 | 42 |
| 4.0 | 2093 | 20 |
| 5.0 | 2262 | 14 |
| 6.0 | 2197 | 13 |
| 7.0 | 2013 | 13 |
| 8.0 | 1837 | 16 |
| 9.0 | 1670 | 16 |
| 10.0 | 1509 | 25 |
| 12.0 | 1189 | 30 |
| 13.0 | 1092 | 24 |
| 14.0 | 998 | 25 |
| 15.0 | 846 | 28 |
| 16.0 | 760 | 26 |
| 18.0 | 593 | 26 |
| 20.0 | 468 | 29 |
| 24.0 | 326 | 37 |
| 30.0 | 162 | 28 |
| 36.0 | 75 | 28 |

Example 2

Pregabalin Controlled Extended Release and Orphenadrine Citrate Immediate Release Capsules Step 1. Manufacturing of Orphenadrine Citrate Immediate Release Beads The Orphenadrine citrate Immediate Release (IR) beads with formula shown below was manufactured using a powder solution layering technique to give a drug load with a potency of about 70%.

| Ingredients | g | Kg |
|---|---|---|
| Orphenadrine citrate | 700.00 | 35 |
| Microcrystalline cellulose | 292.50 | 14.625 |
| Talc | 2.50 | 0.125 |
| Sodium lauryl sulphate | 5.0 | 0.25 |
| Water | QS | QS |
| Total | 1000.00 | 50 |

The materials were charged into a planetary mixer and blended for about 5 minutes. The homogeneous blend was granulated for about 3 minutes with a sufficient quantity of water. The wet mass was extruded using a Caleva extruder Model 25. The extrudates were spheronised in 500 g quantities in a Caleva spheroniser Model 240. The wet spheroids were dried at 40° C. in a tray dryer oven to a loss of drying (LOD) of less than about 2%.

Step 2. Manufacturing of Pregabalin Controlled Extended Release and Orphenadrine Citrate Immediate Release Capsules These were made by encapsulating sufficient amounts of pregabalin delayed release beads equivalent to about 30% of the total dose of pregabalin required and sufficient amounts of pregabalin extended release beads equivalent to about 70% of the total dose of pregabalin required (as prepared in Example 1), plus orphenadrine citrate IR beads, into a hard gelatin capsule using a Zanasi 40E encapsulator.

| | Content of pregabalin and Orphenadrine citrate per capsule 165 mg + 25 mg Capsule Fill weights per capsule (mg) |
|---|---|
| *Amount of Pregabalin delayed release beads | 73.9 |
| Amount of Pregabalin extended release beads | 166.4 |
| Orphenadrine citrate immediate release beads | 35.7 |
| Total amount of beads per Capsule | 276.0 |

Figure 4:
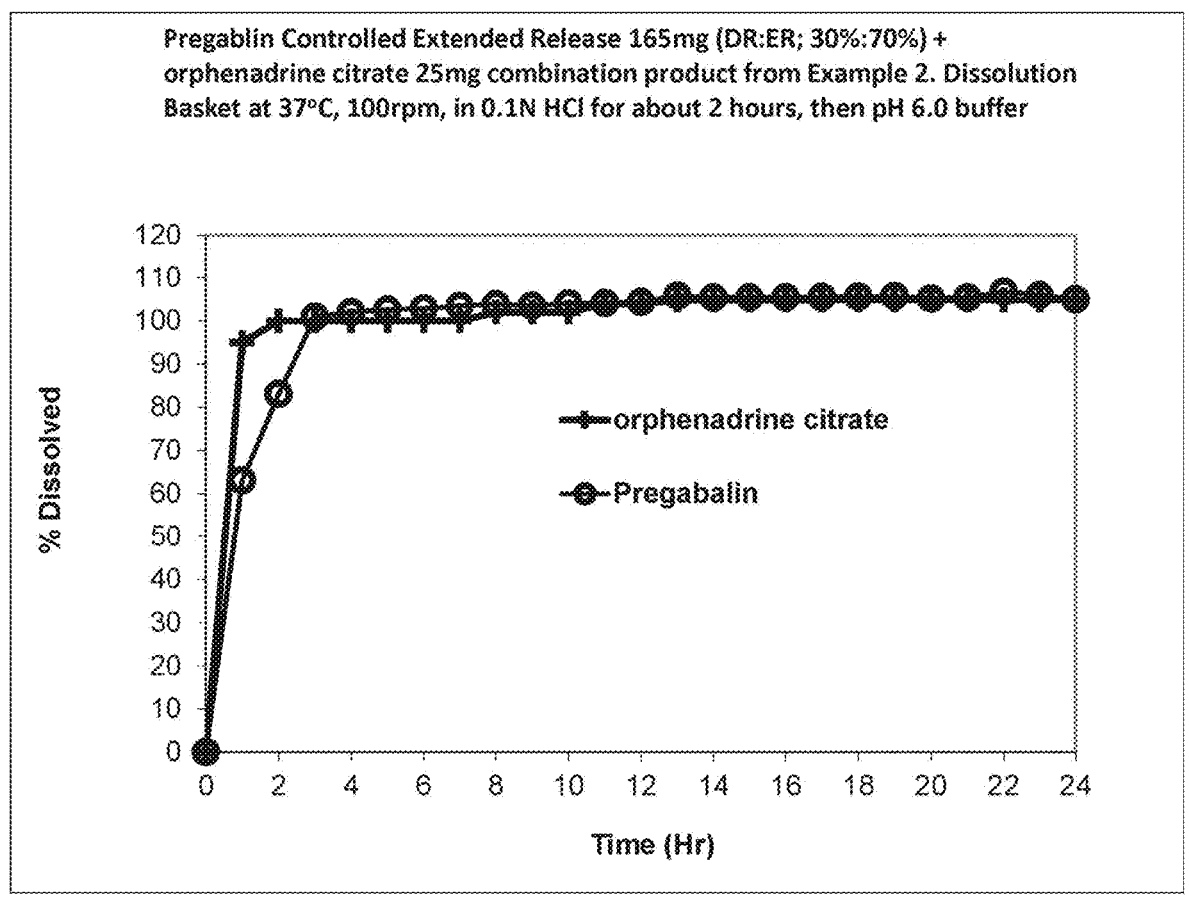
FIG. 4 shows dissolution of 165 mg of pregablin controlled extended release (DR:ER; 30%:70%) and 25 mg of orphenadrine citrate combination product from Example 2, at 37° C., 100 rpm, in 0.1N HCl for about 2 hours, then pH 6.0 buffer.

Results of dissolution studies are shown in FIG. 4.

Example 3

Pregabalin Controlled Extended Release and Methocarbamol Immediate Release Capsules Step 1. Manufacturing of Methocarbamol Immediate Release Beads The Methocarbamol Immediate Release (IR) beads with formula shown below was manufactured using a powder solution layering technique to give a drug load with a potency of about 70%.

| Ingredients | g | Kg |
| --- | --- | --- |
| methocarbamol | 700.00 | 35 |
| Microcrystalline cellulose | 292.50 | 14.625 |
| Talc | 2.50 | 0.125 |
| Sodium lauryl sulphate | 5.0 | 0.25 |
| Water | QS | QS |
| Total | 1000.00 | 50 |

The materials were charged into a planetary mixer and blended for about 5 minutes. The homogeneous blend was granulated for about 3 minutes with sufficient quantity of water.

The wet mass was extruded using a Caleva extruder Model 25. The extrudates were spheronised in 500 g quantities in a Caleva spheroniser Model 240. The wet spheroids were dried at 40° C. in a tray dryer oven to LOD of less than about 2%.

Step 2. Manufacturing of Pregabalin Controlled Extended Release and Methocarbamol Immediate Release Capsules These were made by encapsulating sufficient amounts of Pregabalin delayed release beads equivalent to about 30% of the total dose of pregabalin required and sufficient amounts of Pregabalin extended release beads equivalent to about 70% of the total dose of pregabalin required (as prepared in Example 1), plus Methocarbamol IR beads, into a hard gelatin capsule using a Zanasi 40E encapsulator.

|  | Content of pregabalin and methocarbamol citrate per capsule<br>165 mg + 500 mg Capsule<br>Fill weights per capsule (mg) |
| --- | --- |
| *Amount of Pregabalin delayed release beads | 73.9 |
| Amount of Pregabalin extended release beads | 166.4 |
| Methocarbamol immediate release beads | 714.3 |
| Total amount of beads per Capsule | 954.6 |

Figure 5:
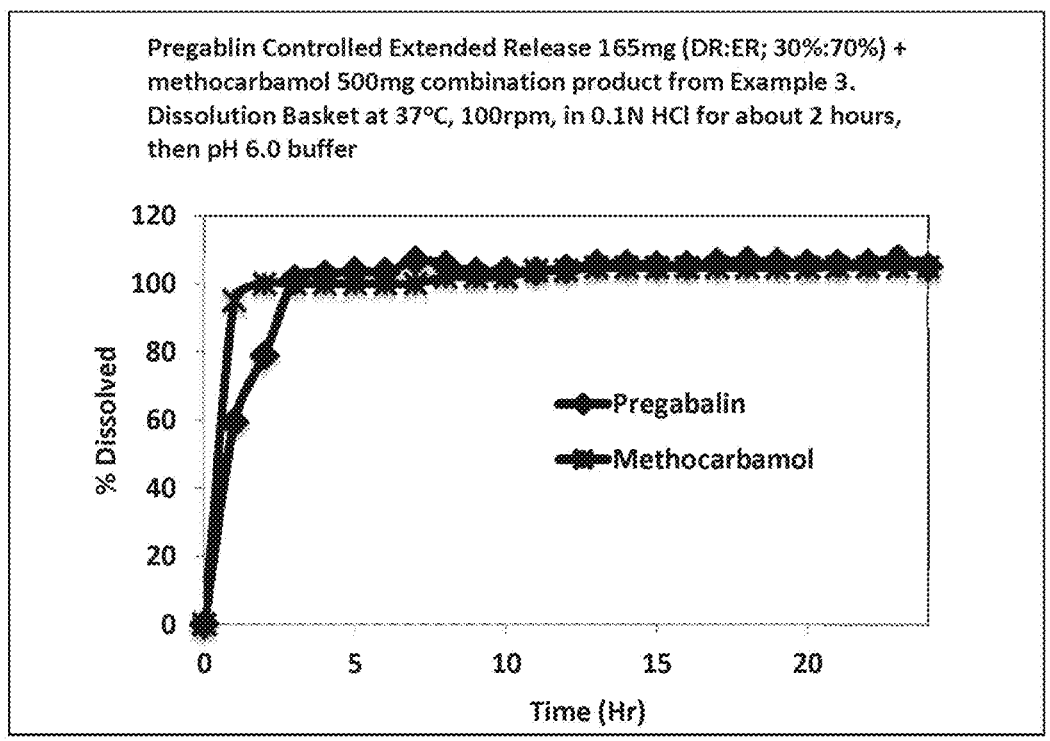
FIG. 5 shows dissolution of 165 mg of pregablin controlled extended release (DR:ER; 30%:70%) and 500 mg of methocarbamol combination product from Example 3, at 37° C., 100 rpm, in 0.1N HCl for about 2 hours, then pH 6.0 buffer.

Results of dissolution studies are shown in FIG. 5.

Example 4

Pregabalin Controlled Extended Release+Aspirin Delayed Release Capsules

Step 1. Manufacturing of Aspirin™ Immediate Release Beads

The Aspirin™ Immediate Release (IR) beads with formula shown below was manufactured using powder solution layering technique to give a drug load with a potency of about 70%.

| Ingredients | g | Kg |
| --- | --- | --- |
| Aspirin ™ | 700.00 | 35 |
| Microcrystalline cellulose | 292.50 | 14.625 |
| Talc | 2.50 | 0.125 |
| Sodium lauryl sulphate | 5.0 | 0.25 |
| Water | QS | QS |
| Total | 1000.00 | 50 |

The materials were charged into a planetary mixer and blended for about 5 minutes. The homogeneous blend was granulated for about 3 minutes with sufficient quantity of water. The wet mass was extruded using a Caleva extruder Model 25. The extrudates were spheronised in 500 g quantities in a Caleva spheroniser Model 240. The wet spheroids were dried at 40° C. in a tray dryer oven to LOD of less than about 2%.

Step 2. Manufacturing of Enteric Coated Aspirin™ Delayed Release (DR) Beads

The Aspirin™ Immediate Release (IR) beads with a potency of about 70% were coated with a pH-dependent coat in a Uni-Glatt fluid bed coater using a Wurster spray technique, to obtain enteric coated Aspirin™ Delayed Release beads.

Preparation of Enteric Coating Suspension

| Ingredients | g |
| --- | --- |
| Aspirin immediate release beads (potency 70%) | 750 |
| Eudragit L | 75.00 |
| Triethyl citrate | 9.00 |
| Talc | 40.00 |
| Simethicone | 3.00 |
| Water* | QS |

*Water is evaporated during coating

An aqueous dispersion of Eudragit L (Methacrylic Acid—Methyl Methacrylate Copolymer [1:1]) was prepared in a stainless steel vessel using a propeller mixer. The dispersion was fluidized in a fluid bed coater and applied using Wurster coating techniques onto immediate release pregabalin beads.

Step 3. Manufacturing of Pregabalin Controlled Extended Release and Aspirin™ Delayed Release Capsules These were made by encapsulating sufficient amounts of pregabalin delayed release beads equivalent to about 30% of the total dose of pregabalin required and sufficient amounts of pregabalin extended release beads equivalent to about 70% of the total dose of pregabalin required (as prepared in Example 1), plus Aspirin™ IR beads into a hard gelatin capsule using a Zanasi 40E encapsulator.

|  | Content of pregabalin and Aspirin ™ per capsule<br>165 mg + 325 mg Capsule<br>Fill weights per capsule (mg) |
| --- | --- |
| *Amount of Pregabalin delayed release beads | 73.9 |
| Amount of Pregabalin extended release beads | 166.4 |
| Aspirin immediate release beads | 542.9 |
| Total amount of beads per Capsule | 783.2 |

Figure 6:
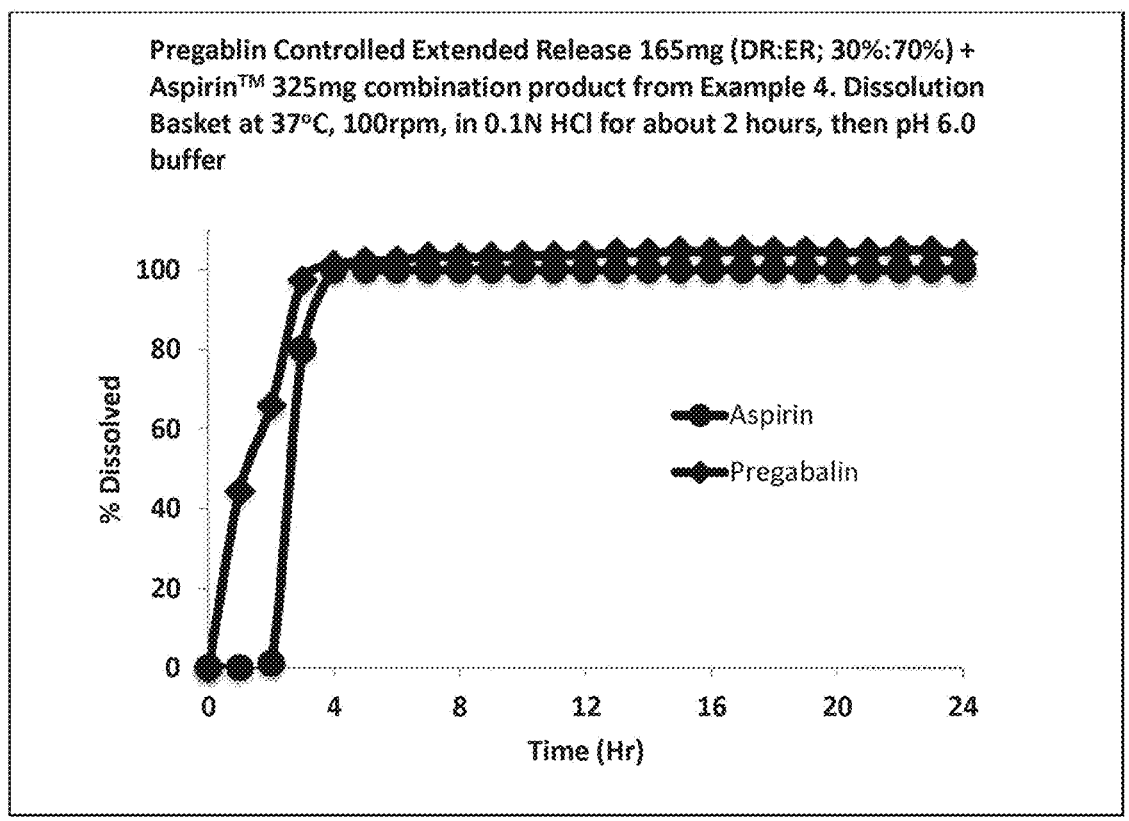
FIG. 6 shows dissolution of 165 mg of pregablin controlled extended release (DR:ER; 30%:70%) and 325 mg of Aspirin™ combination product from Example 4, at 37° C., 100 rpm, in 0.1N HCl for about 2 hours, then pH 6.0 buffer.

Results of dissolution studies are shown in FIG. 6.

Example 5

Pregabalin Controlled Extended Release Capsules

These were made as in Example 1 except that Eudragit L was replaced with Eudragit S.

Example 6

Pregabalin Controlled Extended Release Capsules

These were made as in Example 1 except that Eudragit L was combined with Eudragit S in about equal ratios.

Example 7

Pregabalin Controlled Extended Release Capsules

These were made as in Example 1 except that the ratio of DR:ER was about 20:80 of the total dose of pregabalin.

Example 8

Pregabalin Controlled Extended Release Capsules

These are made as in Example 1 except that the ratio of DR:ER was about 40:60 of the total dose of pregabalin.

Example 9

Pregabalin Controlled Extended Release Capsules

These were made as in Example 1 except that Eudragit L or Eudragit S or their combination was applied as about 2.0% wt/wt of the pregabalin immediate release beads.

Example 10

Pregabalin Controlled Extended Release Capsules

These were made as in Example 1 except that Eudragit L or Eudragit S or their combination was applied as about 10% wt/wt of the pregabalin immediate release beads.

Example 11

Pregabalin Controlled Extended Release Capsules

Step 1. Manufacturing of Preqabalin Immediate Release Beads

The Pregabalin Immediate Release (IR) beads with formula shown below was manufactured using extrusion spheronization technique to give a drug load with a potency of about 60%.

| Ingredients | % | kg/batch |
| --- | --- | --- |
| Microcrystalline cellulose | 35.0 | 35.0 |
| Pregabalin | 60.0 | 60.0 |
| Hydroxypropyl methyl cellulose | 3.0 | 3.0 |
| Sodium lauryl sulphate | 0.5 | 0.5 |
| Crospovidone | 0.5 | 0.5 |
| Talc | 0.5 | 0.5 |
| Silicone dioxide | 0.5 | 0.5 |
| Purified Water USP | QS | QS |
| Total | 100 | 100 |

Step 2. Manufacturing of (pH-Dependent Population) Preqabalin Delayed Release (DR) Beads The Pregabalin Immediate Release (IR) beads with a potency of about 60% was coated with a pH-dependent coat in a Uni-Glatt fluid bed coater using a Wurster spray technique, to obtain (pH-dependent population) Pregabalin Delayed Release beads.

Preparation of pH-dependent Coating Suspension

| Ingredients | g |
| --- | --- |
| Pregabalin immediate release beads (potency 60%) | 1 × 105 |
| Eudragit L | 7500.00 |
| Triethyl citrate | 900.00 |
| Glycerol monostearate | 10.01 |
| Water* | QS |

*Water is evaporated during coating

An aqueous dispersion of Eudragit L (Methacrylic Acid—Methyl Methacrylate Copolymer [1:1]) was prepared in a stainless steel vessel using a propeller mixer. The pregabalin IR beads was fluidized in a fluid bed coater and the dispersion applied using Wurster coating techniques onto the immediate release pregabalin beads.

Step 3. Manufacturing of (pH-independent Population) Pregabalin Extended Release Beads The Pregabalin Immediate Release (IR) beads with a potency of about 60% were coated with a pH-independent coat in a Uni-Glatt fluid bed coater using a Wurster spray technique, to obtain (pH-independent population) Pregabalin Extended Release beads.

Preparation of Ethylcellulose Extended Release Suspension

| Ingredients | g |
| --- | --- |
| Pregabalin immediate release beads (potency 60%) | 500 |
| Ethylcellulose | 15.47 |
| Hydroxypropylmethyl cellulose | 5.63 |
| Triethyl citrate | 1.41 |
| Talc | 1.41 |
| Ethanol* | QS |

*Ethanol is evaporated during coating

An ethanolic suspension of ethylcellulose was prepared in a stainless steel vessel using a high shear mixer. The suspension was fluidized in a fluid bed coater and applied using Wurster coating techniques onto the immediate release pregabalin beads.

Step 4. Manufacturing of Pregabalin Controlled Extended Release (CXR) Capsules

Pregabalin controlled extended release capsules were made by encapsulating sufficient amounts of pregabalin delayed release beads equivalent to about 70% of the total dose of pregabalin required and sufficient amounts of pregabalin extended release beads equivalent to about 30% of the total dose of pregabalin required into a hard gelatin capsule using a Zanasi 40E encapsulator.

| | Content of pregabalin per capsule | | | | | |
|---|---|---|---|---|---|---|
| | 37.5 mg Capsule | 75 mg Capsule | 150 mg Capsule | 300 mg Capsule | 450 mg Capsule | 600 mg Capsule |
| | Fill weights per capsule (mg) | | | | | |
| *Amount of Pregabalin delayed release (DR) beads | 49.1 | 98.3 | 196.6 | 393.3 | 589.9 | 786.5 |
| Amount of Pregabalin extended release (ER) beads | 20.3 | 40.5 | 81.1 | 162.1 | 243.2 | 324.2 |
| Total amount of beads per Capsule | 69.4 | 138.8 | 277.7 | 555.4 | 833.1 | 1110.7 |

Example 12

Pregabalin Controlled Extended Release Capsules

These were made as in Example 11 except that the ratio of DR:ER was about 60:40 of the total dose of pregabalin.

Example 13

Pregabalin Controlled Extended Release Capsules

These were made as in Example 11 except that the ratio of DR:ER was about 50:50 of the total dose of pregabalin.

Example 14

Pregabalin Controlled Extended Release Capsules

These were made as in Example 11 except that the ratio of DR:ER was about 40:60 of the total dose of pregabalin.

Example 15

Pregabalin Controlled Extended Release Capsules

These were made as in Example 11 except that the ratio of DR:ER was about 30:70 of the total dose of pregabalin.

Example 16

Pregabalin Controlled Extended Release Capsules

Step 1. Manufacturing of Pregabalin Immediate Release Beads

The Pregabalin Immediate Release (IR) beads with formula shown below was manufactured using powder solution layering technique in a centrifugal coater to give a drug load with a potency of about 70%.

| Ingredients | g | Kg |
|---|---|---|
| Non Pareil sugar beads | 9.25 | 4.625 |
| Pregabalin | 70.00 | 35 |
| Povidone (PVP K30) | 20.00 | 10 |
| Talc | 0.250 | 0.125 |
| Sodium lauryl sulphate | 0.50 | 0.25 |
| Isopropanol | QS | QS |
| Total | 100.00 | 50 |

Step 2. Manufacturing of (pH-dependent Population) Pregabalin Delayed Release (DR) Beads The Pregabalin Immediate Release (IR) beads with a potency of about 70% were coated with a pH-dependent coat in a Uni-Glatt fluid bed coater using a Wurster spray technique, to obtain (pH-dependent population) Pregabalin Delayed Release beads.

Preparation of pH-dependent Coating Suspension

| Ingredients | g |
|---|---|
| Pregabalin immediate release beads (potency 70%) | 750 |
| Eudragit L | 37.50 |
| Triethyl citrate | 4.50 |
| Talc | 19.75 |
| Simethicone | 1.15 |
| Water* | QS |

*Water is evaporated during coating

An aqueous dispersion of Eudragit L (Methacrylic Acid—Methyl Methacrylate Copolymer [1:1]) was prepared in a stainless steel vessel using a propeller mixer. The dispersion was fluidized in a fluid bed coater and applied using Wurster coating techniques onto the immediate release pregabalin beads.

Step 3. Manufacturing of (pH-independent Population) Pregabalin Extended Release Beads The Pregabalin Immediate Release (IR) beads with a potency of about 70% were coated with a pH-independent coat in a Uni-Glatt fluid bed coater using a Wurster spray technique, to obtain (pH-independent population) Pregabalin Extended Release beads.

Preparation of Ethylcellulose Extended Release Suspension

| Ingredients | g |
|---|---|
| Pregabalin immediate release beads (potency 70%) | 800 |
| Ethylcellulose | 16.50 |
| Hydroxypropylmethyl cellulose | 6.00 |
| Triethyl citrate | 1.50 |
| Talc | 1.50 |
| Ethanol* | QS |

*Ethanol is evaporated during coating

An ethanolic suspension of ethylcellulose was prepared in a stainless steel vessel using a high shear mixer. The suspension was fluidized in a fluid bed coater and applied using Wurster coating techniques onto the immediate release pregabalin beads.

Step 4. Manufacturing of Pregabalin Controlled Extended Release (CXR) Capsules

Three types of Pregabalin controlled extended release 150 mg capsules (T1, T2, and T3) were made by encapsulating sufficient amounts of pregabalin delayed release beads (potency 67%) and sufficient amounts of pregabalin extended release beads (potency 69.4) equivalent to about 150 mg of the total dose of pregabalin required into a hard gelatin capsule using a Zanasi 40E encapsulator. For T1 the DR:ER ratio is 40:60, for T2 the DR:ER ratio is 30:70, and, for T3 the DR:ER ratio is 50:50, Three types of Pregabalin controlled extended release 150 mg capsules (T1, T2, and T3)

| | Content of pregabalin per capsule | | |
|---|---|---|---|
| | T1 (DR:ER :: 40:60) 150 mg Capsule | T2 (DR:ER :: 30:70) 150 mg Capsule | T3 (DR:ER :: 50:50) 150 mg Capsule |
| | Fill weights per capsule (mg) | | |
| *Amount of Pregabalin delayed release beads | 89.6 | 67.2 | 111.9 |
| Amount of Pregabalin extended release beads | 130.1 | 151.7 | 108.4 |
| Total amount of beads per Capsule | 219.6 | 218.9 | 220.3 |

TABLE 7

Shows an open label, randomised, cross over, comparative oral bioavailability study of Pregabalin XR Capsules 150 mg (Lots; T1, T2 and T3) of Example 16 in normal healthy, adult, human subjects under fasting conditions.

| Description (Pregabalin) | Cmax | AUC(0-t) | AUC(0-∞) | *Tmax |
|---|---|---|---|---|
| Pregabalin XR 150 mg (T1) | | | | |
| N | 12 | 12 | 12 | 12 |
| Mean | 2760.182 | 22874.354 | 24218.290 | 2.00 |
| CV (%) | 22.8 | 28.4 | 28.8 | 51.1 |
| Pregabalin XR 150 mg (T2) | | | | |
| N | 12 | 12 | 12 | 12 |
| Mean | 2136.018 | 19703.316 | 21192.906 | 2.00 |
| CV (%) | 16.2 | 30.1 | 29.3 | 42.0 |
| Pregabalin XR 150 mg (T3) | | | | |
| N | 12 | 12 | 12 | 12 |
| Mean | 2967.171 | 25486.452 | 27038.960 | 2.00 |
| CV (%) | 23.5 | 29.6 | 30.3 | 46.1 |

What is claimed is:

1. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the at least one pH dependent unit dosage form comprises about 30% of a total dose of pregabalin and the at least one pH independent unit dosage form comprises about 70% of the total dose of pregabalin, wherein the composition comprises about 165 mg of API, and wherein on once daily dosing with meals, the plasma concentrations in the following table ±30% are obtained, and time to maximum concentration is 5.0±40%, half life is 6.0±40% and rate at which said at least one API is removed from the body is 0.1±40%:

| Time (Hours) | Mean Plasma Test (ng/mL) | Coefficient of Variation Test (ng/mL) |
|---|---|---|
| 0 | 0 | Missing |
| 0.5 | 13 | 332 |
| 1.0 | 165 | 108 |
| 1.5 | 356 | 93 |
| 2.0 | 706 | 83 |
| 2.5 | 1209 | 46 |
| 3.0 | 1692 | 42 |
| 4.0 | 2093 | 20 |
| 5.0 | 2262 | 14 |
| 6.0 | 2197 | 13 |
| 7.0 | 2013 | 13 |
| 8.0 | 1837 | 16 |
| 9.0 | 1670 | 16 |
| 10.0 | 1509 | 25 |
| 12.0 | 1189 | 30 |
| 13.0 | 1092 | 24 |
| 14.0 | 998 | 25 |
| 15.0 | 846 | 28 |
| 16.0 | 760 | 26 |
| 18.0 | 593 | 26 |
| 20.0 | 468 | 29 |
| 24.0 | 326 | 37 |
| 30.0 | 162 | 28 |
| 36.0 | 75 | 28. |

2. The composition of claim 1, further comprising at least one other API, wherein the at least one other API is in the same unit dosage form(s) as the unit dosage form(s) comprising the at least one API or in a separate unit dosage form(s).

3. The composition of claim 2, wherein the at least one other API is selected from the group consisting of antidepressants, muscle relaxants, antispasmodics, narcotic analgesics, non steroidal anti-inflammatory agents, nerve stimulants, methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

4. The composition of claim 1, wherein said at least one API comprises at least one of pregabalin, a base thereof, and a pharmaceutically acceptable salt thereof.

5. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the at least one pH dependent unit dosage form comprises about 30% of a total dose of pregabalin and the at least one pH independent dosage form comprises about 70% of the total dose of pregabalin, wherein the composition comprises about 165 mg of API and wherein, on once daily dosing without meals, the plasma concentrations in the following table ±40% are obtained, and time to maximum concentration is 3.0±40%, half life is 7.2±40% and rate at which said at least one API is removed from the body is 0.1±40%:

| Time (Hours) | Mean Plasma Test (ng/mL) | Coefficient of Variation Test (ng/mL) |
|---|---|---|
| 0.0 | 0 | Missing |
| 0.5 | 616 | 96 |
| 1.0 | 1590 | 48 |
| 1.5 | 1811 | 43 |
| 2.0 | 2100 | 32 |
| 2.5 | 2237 | 24 |
| 3.0 | 2504 | 21 |
| 4.0 | 2484 | 14 |
| 5.0 | 2216 | 23 |
| 6.0 | 1845 | 20 |
| 7.0 | 1700 | 26 |
| 8.0 | 1523 | 25 |
| 9.0 | 1348 | 28 |
| 10.0 | 1188 | 30 |
| 12.0 | 863 | 23 |
| 13.0 | 834 | 40 |
| 14.0 | 751 | 39 |
| 15.0 | 621 | 40 |
| 16.0 | 554 | 46 |
| 18.0 | 449 | 46 |
| 20.00 | 417 | 50 |
| 24.00 | 291 | 56 |
| 30.00 | 190 | 75 |
| 36.00 | 90 | 58. |

6. The composition of claim 5, further comprising at least one other API, wherein the at least one other API is in the same unit dosage form(s) as the unit dosage form(s) comprising the at least one API or in a separate unit dosage form(s).

7. The composition of claim 6, wherein the at least one other API is selected from the group consisting of antidepressants, muscle relaxants, antispasmodics, narcotic, analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

8. The composition of claim 5, wherein said at least one API comprises at least one of pregabalin, a base thereof, and a pharmaceutically acceptable salt thereof.

9. A controller extended release composition comprising at least two unit dosage forms, the at least two unit dosage forms comprising at least one PH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, pharmaceutically acceptable hydrate thereof, a pharmaceutically acceptable solvate thereof, an enantiomer thereof and a racemate thereof, wherein the composition provides chronotherapeutic, controlled extended release, wherein the at least one pH dependent unit dosage form comprises about 30% of a total dose of pregabalin and the at least one pH independent dosage form comprises about 70% of the total dose of pregabalin, wherein the composition comprises about 165 mg of API and wherein, on once daily multiple dosing steady state without meals, the plasma concentrations in the following table ±30% are obtained, and time to maximum concentration is 98.5±40%, minimum concentration is 91.0±40% and average concentration is 1088±40%:

| Time (Hours) | Mean Plasma Test (ng/mL) | Coefficient of Variation Test (ng/mL) |
|---|---|---|
| 0.0 | 0.0 | Missing |
| 24.0 | 272 | 31 |
| 48.0 | 296 | 32 |
| 72.0 | 296 | 29 |
| 96.0 | 293 | 31 |
| 96.5 | 798 | 80 |
| 97.0 | 2070 | 51 |
| 97.5 | 2863 | 32 |
| 98.0 | 3189 | 24 |
| 98.5 | 3136 | 15 |
| 99.0 | 3053 | 14 |
| 100.0 | 2860 | 14 |
| 101.0 | 2489 | 18 |
| 102.0 | 2115 | 20 |
| 103.0 | 1755 | 24 |
| 104.0 | 1743 | 19 |
| 105.0 | 1594 | 17 |
| 106.0 | 1421 | 20 |
| 108.0 | 1110 | 22 |
| 109.0 | 995 | 22 |
| 110.0 | 870 | 25 |
| 111.0 | 780 | 23 |
| 112.0 | 682 | 25 |
| 114.0 | 508 | 26 |
| 116.0 | 410 | 30 |
| 120.0 | 282 | 30 |
| 126.0 | 143 | 37 |
| 132.0 | 91 | 52. |

10. The composition of claim 9, further comprising at least one other API, wherein the at least one other API is in the same unit dosage form(s) as the unit dosage form(s) comprising the at least one API or in a separate unit dosage form(s).

11. The composition of claim 10, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, ibuprofen, toradol, naproxen, diclofenac sodium, and combinations thereof.

12. The composition of claim 9, wherein said at least one API comprises at least one of pregabalin, a base thereof, and a pharmaceutically acceptable salt thereof.

13. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof wherein the composition provides chronotherapeutic controlled extended release, wherein the at least one pH dependent unit dosage form comprises about 30% of a total dose of pregabalin and the at least one pH independent dosage form comprises about 70% of the total dose of pregabalin, wherein the composition comprises about 82.5mg of API and wherein, on twice daily dosing without meals, the plasma concentrations In the following table ±4.0% are obtained, and time to maximum concentration is 14.0±40%, half life is 7.1±40% and rate at which said at least one API is removed from the body is 0.1±40%:

| Time (Hours) | Mean Plasma Test (ng/mL) | Coefficient of Variation Test (ng/mL) |
|---|---|---|
| 0.0 | 0.0 | Missing |
| 0.5 | 134 | 106 |
| 1.0 | 972 | 41 |
| 1.5 | 1220 | 34 |
| 2.0 | 1161 | 19 |
| 2.5 | 1182 | 18 |
| 3.0 | 1166 | 25 |
| 4.0 | 1145 | 26 |
| 5.0 | 1023 | 21 |
| 6.0 | 896 | 27 |
| 7.0 | 830 | 31 |
| 8.0 | 716 | 27 |
| 9.0 | 620 | 30 |
| 10.0 | 543 | 30 |
| 12.0 | 440 | 28 |
| 13.0 | 1134 | 49 |
| 14.0 | 1754 | 17 |
| 15.0 | 1653 | 20 |
| 16.0 | 1582 | 29 |
| 18.0 | 1240 | 24 |
| 20.0 | 991.5 | 30 |
| 24.0 | 713 | 29 |
| 30.0 | 417 | 35 |
| 36.0 | 217 | 35. |

14. The composition of claim 13, further comprising at, least one other API, wherein the at least one other API is in the same, unit dosage, form(s) as the unit dosage form(s) comprising the at least one API or in a separate unit dosage form(s).

15. The composition of claim 14, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

16. The composition of claim 13, wherein said at least one API comprises at least one of pregabalin, a base thereof, and a pharmaceutically acceptable salt thereof.

17. A controlled extended release composition comprising at least two unit dosage forms, the at least two unit dosage forms comprising, at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, pharmaceutically acceptable hydrate thereof, a pharmaceutically acceptable solvate thereof, an enantiomer thereof and a racemate thereof, wherein the composition provides chronotherapeutic controlled extended release, wherein the at least one pH dependent unit dosage form comprises about 30% of a total dose of pregabalin and, the at least one pH independent dosage form comprises about 70% of the total dose of pregabalin, wherein the composition Comprises about 82.5 mg of API and wherein, on twice daily dosing with meal, the plasma concentrations in the following table ±40% are obtained, and time to maximum concentration is 14.0±40%, half life is 5.9±40% and rate at which said at least one API is removed from the body is 0.1±40%:

| Time (Hours) | Mean Plasma Test (ng/mL) | Coefficient of Variation Test (ng/mL) |
|---|---|---|
| 0.0 | 0 | Missing |
| 0.5 | 4 | 346 |
| 1.0 | 56 | 219 |
| 1.5 | 177 | 114 |
| 2.0 | 433 | 64 |
| 2.5 | 561 | 56 |
| 3.0 | 728 | 49 |
| 4.0 | 1155 | 43 |
| 5.0 | 1332 | 23 |
| 6.0 | 1170 | 18 |
| 7.0 | 1075 | 18 |
| 8.0 | 999 | 19 |
| 9.0 | 924 | 27 |
| 10.0 | 837 | 26 |
| 12.0 | 642 | 29 |
| 13.0 | 1450 | 31 |
| 14.0 | 1956 | 20 |
| 15.0 | 1918 | 22 |
| 16.0 | 1649 | 25 |
| 18.0 | 1370 | 23 |
| 20.0 | 1078 | 21 |
| 24.0 | 765 | 26 |
| 30.0 | 383 | 24 |
| 36.0 | 178 | 31. |

18. The composition of claim 17, further comprising at least one other API, wherein the at least one other API is in the same unit dosage form(s) as the unit dosage form(s) comprising the at least one API, or in a separate unit dosage form(s).

19. The composition of claim 18, wherein the at least one other API is selected from the group consisting of antidepressants, muscle relaxants, antispasmodics, narcotic analgesics, non steroidal anti-inflammatory agents, nerve, stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

20. The composition of claim 17, wherein said at least one API comprises at least one of pregabalin, a base thereof, and a pharmaceutically acceptable salt thereof.

21. A. controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof wherein the composition provides chronotherapeutic controlled extended release, wherein the at least one pH dependent unit dosage form comprises about 30% of a total dose of pregabalin and the at least one pH independent dosage form comprises about 70% of the total dose of pregabalin, wherein the composition comprises about 82.5mg of API and wherein, on once daily multiple dosing steady state without meals, the plasma concentrations in the following table ±40% are obtained, and time to maximum concentration is 111.0±40%, minimum concentration is 274.5±40% and average concentration is 1041±40%:

| Time (Hours) | Mean Plasma Test (ng/mL) | Coefficient of Variation Test (ng/mL) |
|---|---|---|
| 0.0 | 0.0 | Missing |
| 24.0 | 756 | 18 |
| 48.0 | 887 | 26 |
| 72.0 | 889 | 22 |
| 96.0 | 836 | 22 |
| 96.5 | 936 | 16 |
| 97.0 | 1436 | 29 |
| 97.5 | 1636 | 25 |
| 98.0 | 1639 | 20 |
| 98.5 | 1703 | 18 |
| 99.0 | 1776 | 17 |
| 100.0 | 1647 | 21 |
| 101.0 | 1495 | 22 |
| 102.0 | 1338 | 22 |
| 103.0 | 1207 | 27 |
| 104.0 | 1077 | 24 |
| 105.0 | 945 | 26 |
| 106.0 | 842 | 24 |
| 108.0 | 636 | 25 |
| 109.0 | 1016 | 40 |
| 110.0 | 1784 | 27 |
| 111.0 | 2311 | 16 |
| 112.0 | 1948 | 15 |
| 114.0 | 1576 | 21 |
| 116.0 | 1206 | 19 |
| 120.0 | 844 | 18 |
| 126.0 | 417 | 24 |
| 132.0 | 274 | 28. |

22. The composition of claim 21, further comprising at least one other API, wherein the at least one other API is in the same unit dosage form(s) as the unit dosage form(s) comprising the at least one API or in a separate unit dosage form(s).

23. The composition of claim 22, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, imipramine, Asprin, ibuprofen, toradol, naproxen, diclofenac sodium, and combinations thereof.

24. The composition of claim 21, wherein said at least one API comprises at least one of pregabalin, a base thereof, and a pharmaceutically acceptable salt thereof.

25. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least One pH independent coat, wherein the core of each of the unit ,dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the composition has the following dissolution time-percent release profile based on an initial 70% of API in the core of each of the at least one pH dependent unit dosage form and the at least one pH independent unit dosage form:

| Time [Min] | % Pregabalin released |
|---|---|
| 0 | 0 |
| 60 | 41 ± 30% |
| 70 | 73 ± 30% |
| 80 | 75 ± 25% |
| 90 | 77 ± 25% |
| 120 | 80 ± 25% |
| 150 | 83 ± 10% |
| 180 | 85 ± 10% |
| 240 | 89 ± 10% |
| 300 | 92 ± 10% |
| 360 | 94 ± 10%. |

26. The composition of claim 25, Rather comprising at least one other API, wherein the at least one other API is in the same unit dosage form(s) as the unit dosage form(s) comprising the at least one API or in a separate unit dosage form(s).

27. The composition of claim 26, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

28. The composition of claim 25, wherein said at least one API comprises at least one of pregabalin, a base thereof, and a pharmaceutically acceptable salt thereof.

29. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the at least one pH dependent unit dosage form has the following dissolution time-percent released profile based on an initial 70% of API in the core of the at least one pH dependent unit dosage form:

| Time [Hr] | % Pregabalin released |
|---|---|
| 0 | 0 |
| 1 | 20 ± 30% |
| 2 | 43 ± 30% |
| 3 | 102 ± 10% |
| 4 | 105 ± 10% |
| 5 | 106.0 ± 10% |
| 6 | 106 ± 10% |
| 7 | 106 ± 10% |
| 8 | 107 ± 10%. |

30. The composition of claim 29 further comprising at least one other API, wherein the at least one other API is in the same unit dosage form( )as the unit dosage form(s) comprising the at least one API or in a separate unit dosage form(s).

31. The composition of claim 30, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, baclofen, Carisoprodel, Chlorzoxazone, Dantrolene, Methocarbamol, Orphenadrine, Tizanidine, imipramine, Asprin, ibuprofen, toradol, naproxen, diclofenac sodium, and combinations thereof.

32. The composition of claim 29, wherein said at least one API comprises at least one of pregabalin, a base thereof, and a pharmaceutically acceptable salt thereof.

33. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the at least one pH independent unit dosage form has the following dissolution time-percent released profile based on an initial 70% of API in the core of the at least one pH independent unit dosage form:

| Time [Hr] | % Pregabalin released |
|---|---|
| 0 | 0 |
| 1 | 63 ± 30% |
| 2 | 82 ± 30% |
| 3 | 91 ± 10% |
| 4 | 97 ± 10% |
| 5 | 101 ± 10% |
| 6 | 102 ± 10% |
| 7 | 103 ± 10% |
| 8 | 104 ± 10% |
| 9 | 105 ± 10% |
| 10 | 105 ± 10% |
| 11 | 105 ± 10% |
| 12 | 107 ± 10%. |

34. The composition of claim 33, further comprising at least one other API, wherein the at least one other API is in the same unit dosage form(s) as the unit dosage form(s) comprising the at least one API or in a separate unit dosage form(s).

35. New The composition of claim 34, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

36. The composition of claim 33, wherein said at least one API comprises at least one of pregabalin, a base thereof, and a pharmaceutically acceptable salt thereof.

37. a controlled extended release composition comprising, at least two unit dosage forms, the at least unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one, active pharmaceutical ingredient (API), wherein said at least one API comprises at least one of pregabalin, a base thereof, pharmaceutically acceptable prodrug thereof, a pharmaceutically acceptable derivative thereof, a pharmaceutically acceptable complex thereof, pharmaceutically acceptable salt thereof, a pharmaceutically acceptable polymorph thereof a pharmaceutically acceptable hydrate thereof, a pharmaceutically acceptable solvate thereof, an enantiomer thereof and a racemate thereof, wherein the composition provides chronotherapeutic controlled extended release, wherein the at least one pH dependent unit dosage form has the following dissolution time-percent released profile based on an initial 60% of API in the core of the at least one pH dependent unit dosage form:

| Time [Hr] | % Pregabalin released |
|---|---|
| 0 | 0 |
| 1 | 12 ± 30% |
| 2 | 41 ± 30% |
| 3 | 95 ± 15% |
| 4 | 98 ± 10%. |

38. The composition of claim 37, further comprising at least one other API, wherein the at least one other API is in the same unit dosage form(s) as the unit dosage form(s) comprising the at least one API or in a separate unit dosage form(s).

39. The composition of claim 38, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

40. The composition of claim 37, wherein said at least one API comprises at least one of pregabalin, a base thereof, and a pharmaceutically acceptable salt thereof.

41. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof pharmaceutically acceptable polymorph thereof, a pharmaceutically acceptable hydrate thereof, a pharmaceutically acceptable solvate thereof, an enantiomer thereof and a racemate thereof, wherein the composition provides chronotherapeutic controlled extended release, wherein the at least one pH independent unit dosage form has the following dissolution time-percent released profile based on an initial 60% of API in the core of the at least one pH independent unit dosage form:

| Time [Hr] | % Pregabalin released |
|---|---|
| 0 | 0 |
| 1 | 74 ± 20% |
| 2 | 89 ± 15% |
| 3 | 93 ± 15% |
| 4 | 94 ± 15% |
| 5 | 95 ± 15%. |

42. The composition of claim 41, further comprising at least one other API, wherein the at least one other API is in the same unit dosage form(s) as the unit dosage form(s) comprising the at least one API or in a separate unit dosage form(s).

43. The composition of claim 42, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

44. The composition of claim 41, wherein said at least one API comprises at least one of pregabalin, a base thereof and a pharmaceutically acceptable salt thereof.

45. A controlled extended release composition comprising at least two unit dosage forms, the at least two unit dosage forms comprising at least one pH dependent unit dosage form comprising a core and at least one pH dependent coat, and at least one pH independent unit dosage form comprising a core and at least one pH independent coat, wherein the core of each of the unit dosage forms comprises at least one active pharmaceutical ingredient (API), wherein said at least one API comprises at least one of pregabalin, a base thereof, a pharmaceutically acceptable prodrug thereof, a pharmaceutically acceptable derivative thereof, a pharmaceutically acceptable complex thereof, a pharmaceutically acceptable salt thereof, a pharmaceutically acceptable polymorph thereof, a pharmaceutically acceptable hydrate thereof, a pharmaceutically acceptable solvate thereof, enantiomer thereof and a racemate thereof, wherein the composition provides chronotherapeutic controlled extended release, wherein the at least one pH dependent unit dosage form comprises about 70% of a total dose of pregabalin and the at least one pH independent dosage form comprises about 30% of the total dose of pregabalin, wherein the composition has the following dissolution time-percent released profile:

| Time [Hr] | % Pregabalin released |
|---|---|
| 0 | 0 |
| 1 | 52 ± 30% |
| 2 | 80 ± 30% |
| 3 | 97 ± 25% |
| 4 | 97 ± 20% |
| 5 | 97 ± 10% |
| 6 | 98 ± 10%. |

46. The composition of claim 45, further comprising at least one other API, wherein the at least one other API is in the same unit dosage form(s) as the unit dosage form(s) comprising the at least one API or in a separate unit dosage form(s).

47. The composition of claim 46, wherein the at least one other API is selected from the group consisting of antidepressants, muscle relaxants, antispasmodics, narcotic analgesics, non steroidal anti-inflammatory agents, nerve stimulants, Methylcobalamine, Oxycodone, Hydrocodone, Oxymorphine, Celecoxib, paracetamol, rofecoxib, cyclobenzaprine, metaxalone, Baclofen, Carisoprodol, Chlorzoxazone, Dantrolene, Methocarbamol, Orphenadrine, Tizanidine, imipramine, Asprin, ibuprofen, toradol, naproxen, diclofenac sodium, and combinations thereof.

48. The composition of claim 45, wherein said at least one API comprises at least one of pregabalin, a base thereof, and a pharmaceutically acceptable salt thereof.

* * * * *